(12) United States Patent
Pero

(10) Patent No.: US 7,947,312 B2
(45) Date of Patent: *May 24, 2011

(54) METHOD OF PREPARATION AND COMPOSITION OF A WATER SOLUBLE EXTRACT OF THE BIOACTIVE COMPONENT OF THE PLANT SPECIES UNCARIA FOR ENHANCING IMMUNE, ANTI-INFLAMMATORY, ANTI-TUMOR AND DNA REPAIR PROCESSES OF WARM BLOODED ANIMALS

(76) Inventor: Ronald W. Pero, Arlington, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/473,396

(22) Filed: May 28, 2009

(65) Prior Publication Data

US 2009/0298939 A1 Dec. 3, 2009

Related U.S. Application Data

(63) Continuation of application No. 10/970,144, filed on Oct. 21, 2004, now Pat. No. 7,595,064, which is a continuation-in-part of application No. 10/093,794, filed on Mar. 7, 2002, now Pat. No. 6,964,784.

(51) Int. Cl.
*A61K 36/00* (2006.01)
*A61K 31/34* (2006.01)
*A61K 31/05* (2006.01)

(52) U.S. Cl. ......... 424/725; 514/470; 514/731; 514/732

(58) Field of Classification Search .................. None
See application file for complete search history.

(56) References Cited

U.S. PATENT DOCUMENTS

| | | | | |
|---|---|---|---|---|
| 4,363,815 A * | 12/1982 | Yu et al. | ................... | 514/263.31 |
| 4,940,803 A * | 7/1990 | Mills et al. | ................... | 549/302 |
| 5,401,858 A * | 3/1995 | Huynh-Ba | ................... | 549/302 |
| 5,589,505 A * | 12/1996 | Yu et al. | ................... | 514/470 |
| 5,656,665 A * | 8/1997 | Yu et al. | ................... | 514/557 |
| 6,039,949 A * | 3/2000 | Pero | ................... | 424/769 |
| 6,111,132 A * | 8/2000 | Kim et al. | ................... | 560/125 |
| 6,225,341 B1 * | 5/2001 | Bischofberger et al. | ...... | 514/459 |
| 6,238,675 B1 * | 5/2001 | Pero | ................... | 424/775 |
| 6,693,128 B2 * | 2/2004 | de Paulis et al. | ............. | 514/473 |
| 7,595,064 B2 * | 9/2009 | Pero | ................... | 424/725 |

OTHER PUBLICATIONS

Adamson et al. Biochem. J. 1969, vol. 112, No. I 1, p. 17P.*
Sheng et al. J. Ethnopharmacol. 2000. vol. 69, pp. 115-126.*
Akesson et al. Intl. Immunopharmacol. 2005. vol. 5, pp. 219-229.*

* cited by examiner

*Primary Examiner* — Christopher R. Tate
(74) *Attorney, Agent, or Firm* — David W. Danenberg; Davidoff Malito & Hutcher LLP

(57) ABSTRACT

The disclosure provides a method for isolating the bioactive component of the water-soluble extract of *Uncaria tomentosa* known as C-MED-100®, comprising (i) precipitating the spray drying carrier from C-MED-100®; (ii) using the resulting C-MED-100® to obtain a spotting mixture for thin layer chromatography (TLC); (iii) spotting the C-MED-100® spotting mixture on pre-run TLC plates and eluting the plates to obtain the fluorescing band with $R_f=0.2-0.3$; (iv) scraping off the $R_f=0.2-0.3$ band, eluting it in ammonia and freeze drying the eluted band to form a powder; and (v) extracting the powder with methanol to remove solubilized silica gel, concentrating the methanol solution and crystallizing the concentrated solution to obtain the bioactive component. The isolated bioactive component in vitro is a quinic acid analog, preferably quinic acid lactone. By contrast, the disclosure further shows the isolated bioactive component in vivo is quinic acid, whether as free acid or as a quinic acid salt, including quinic acid ammonium salt. The disclosure then provides for a pharmaceutical composition comprising a pharmaceutically effective amount of the bioactive component and a nontoxic inert carrier or diluent. The pharmaceutical composition and bioactive component may be used to enhance immune competency, treat disorders associated with the immune system, inhibit the inflammatory response, treat disorders associated with the inflammatory response, enhance the anti-tumor response, and treat disorders associated with the response to tumor formation and growth, all in mammals.

10 Claims, 10 Drawing Sheets

In vitro growth inhibition induced by various quinic acid salts in cultured HL-60 cells

METHOD OF PREPARATION AND COMPOSITION OF A WATER SOLUBLE EXTRACT OF THE BIOACTIVE COMPONENT OF THE PLANT SPECIES UNCARIA FOR ENHANCING IMMUNE, ANTI-INFLAMMATORY, ANTI-TUMOR AND DNA REPAIR PROCESSES OF WARM BLOODED ANIMALS

CROSS-REFERENCE TO RELATED APPLICATIONS

This application is a continuation of U.S. patent application Ser. No. 10/970,144 to Pero, filed Oct. 21, 2004, and allowed Jan. 30, 2009 which, in turn, is a continuation-in-part of U.S. patent application Ser. No. 10/093,794 to Pero, filed Mar. 7, 2002, patented as U.S. Pat. No. 6,964,784 on Nov. 15, 2005, and incorporates its subject matter herein by reference in its entirety. These applications and patents are assigned to Optigenex, Inc.

BACKGROUND OF THE INVENTION

1. Field of the Invention

The present invention is directed to the isolation, purification and structural identification of the bioactive component of water extracts of Cat's Claw (*Uncaria* species). The bioactive component previously was identified in vitro as quinic acid lactone and other related quinic acid esters. The present invention now identifies the in vivo bioactive component as quinic acid and quinic acid salts, including quinic acid ammonium salts. The present invention also is directed to the pharmaceutical use of said bioactive component for enhancing the immune, anti-inflammatory, anti-aging, anti-tumor and DNA repair processes in warm blooded animals.

2. Discussion of the Related Art

*Uncaria tomentosa*, commonly known as Una de Gato or Cat's Claw, has been widely used historically as a natural remedy, and is currently present in a number of nutritional formulations to treat a large variety of health disorders. To applicant's knowledge, all of the commercial preparations of Cat's Claw except the water soluble extract (the "Pero extract") disclosed in U.S. Pat. Nos. 6,039,949 and 6,238,675 B1 and allowed patent U.S. Ser. No. 09/824,508, issued as U.S. Pat. No. 6,361,805 B2 (the "Pero patents") to Pero, and U.S. Pat. No. 6,797,286 to Bobrowski, are based on the oxindole alkaloid content thereof. This is due to Dr. Keplinger's (Austria) discovery, in the early 1960's, of the presence of oxindole alkaloids. (Keplinger, K., Laus, G., Wurm, M., Dierich, M. P., Teppner, H., "*Uncaria tomentosa* (Willd.) DC.- Ethnomedicinal use and new pharmacological, toxicological and botanical results," J. Ethanopharmacology 64:23-34, 1999). The Pero extract, the preferred embodiment of which is commercially available under the names C-MED-100® and ACTIVAR AC-11™, is a novel Cat's Claw extract quite unlike any other commercial versions in that it contains only traces of alkaloids (<0.05%) (Sheng et al., "Treatment of chemotherapy-induced leucopenia in the rat model with aqueous extract from *Uncaria tomentosa*," Pytomedicine 7(2): 137-143, 2000). Instead, the Pero extract contains a new class of active ingredients, carboxyl alkyl esters (CAEs), having demonstrated efficacy as described and protected in the Pero patents. C-MED-100® and ACTIVAR AC-11™ are the first products offered in the nutritional industry to support both auto-immune and DNA repair-enhancing functions, which are of critical importance in reducing the consequences of age-related disorders such as autoimmune, inflammatory and neoplastic diseases. References herein to C-MED-100® and/or ACTIVAR AC-11™ shall be understood to include the Pero extract, of which C-MED-100® and ACTIVAR AC-11™ are preferred embodiments.

The precise chemical identification of the Pero extract's active ingredients has not heretofore been achieved. However, the chemical and biological characteristics of those ingredients have been sufficiently completed to standardize the commercial manufacture of the Pero extract. (See, the Pero patents).

C-MED-100® and ACTIVAR AC-11™, which are the commercially available Pero extract, are formulated and based on the historical medicinal uses of Cat's Claw, of which an important step is exhaustive hot water extraction for approximately 18 hours at around 95° C. The extract is then ultrafiltrated to remove high molecular weight (>10,000 MW) toxic conjugates, and spray dried to contain 8-10% carboxy alkyl esters (CAEs) as active ingredients in vitro. CAEs were characterized as the only active ingredients of C-MED-100® in vitro as a result of their absorption (85%) onto charcoal. No biological activity was observed in the unabsorbed fraction. Using thin layer chromatography (TLC) as the purification tool, the active ingredients showed a UV absorption maximum at about 200 nm, and reacted with hydroxylamine and ferric chloride, thus characterizing them as esters (e.g. CAEs). The inventor has subsequently determined that the active ingredients of C-MED-100® and ACTIVAR AC-11™ in vivo are quinic acid, as free acid, and its salts, including quinic acid ammonium salt. There are two physiological factors regarding the natural forms of quinic acid as the active ingredients of water extracts of Cat's Claw such as C-MED-100® or ACTIVAR AC-11™ which, in turn, might result in quite different biological responses when administered in vitro or in vivo. First, the acidity of the stomach, pH=1, has been shown to be strong enough to hydrolyze any quinic acid esters present in C-MED-100® to quinic acid. Second, the microflora of the digestive tract of mammals are well known to both synthesize and metabolically convert quinic acid to other analogs such as chlorogenic acid, ferrulic acid, shikimic acid, cinnamonic acid, and benzoic acid. (Seifter E., Rettura G., Reissman D., Kambosos D., Levevson S. M. 1971, "Nutritional response to feeding L-phenylacetic, skikimic and D-quinic acids in weanling rats," J. Nutr. 101(6): 747-54; Gonthier M. P., et al. 2003, "Chlorogenic acid bioavailability largely depends on its metabolism by the gut microflora in rats," J. Nutr. 133(6): 1853-63). These well known physiologic facts have raised the possibility that even though quinic acid esters are the bioactive ingredients in vitro, quinic acid esters in vivo could have been metabolized to quinic acid before being absorbed into circulation to mediate efficacious responses. The research disclosed herein confirms that this is the case.

Daily oral doses of C-MED-100® between 250-700 mg have proven efficacious in humans. These dosages have been shown to enhance anti-inflammatory, DNA repair, immuno and anti-tumor processes of warm blooded animals, including humans. (See, the Pero patents; Lamm, S., Sheng, Y., Pero, R. W., "Persistent response to pneumococcal vaccine in individuals supplemented with a novel water soluble extract of *Uncaria tomentosa*, C-Med-100," Phytomed 8: 267-274, 2001; Sheng, Y., Li, L., Holmgren, K., Pero, R. W., "DNA repair enhancement of aqueous extracts of *Uncaria Tomentosa* in a human volunteer study," Phytomed 8: 275-282, 2001; Sheng, Y., Bryngelsson, C., Pero, R. W., "Enhanced DNA repair, immune function and reduced toxicity of C-MED-100™, a novel aqueous extract from *Uncaria tomentosa*," J. of Ethnopharmacology 69:115-126 (2000)).

The CAEs in C-MED-100® are shown to give profound nutritional support as a dietary supplement because the CAEs enhance both DNA repair and immune cell responses, which, in turn, are the critical physiological processes that regulate aging. (See, the Pero patents, Sheng, Y., Pero, R. W., Wagner, H., "Treatment of chemotherapy-induced leukopenia in a rat model with aqueous extract from *Uncaria tomentosa*," Phytomedicine 7(2):137-143 (2000) and as cited above). Both of these processes involve regulating the nuclear transcription factor kappa beta (NF-κB). NF-κB is well known to control (i) the nuclear events that salvage cells from apoptotic cell death and (ii) pro-inflammatory cytokine production. (Beg, A. A. and Baltimore, D., "An essential role for NF-κB in preventing tumor necrosis factor alpha (TNF-α) induced cell death," Science 274: 782-784, 1996; Wang, C-Y, Mayo, M. W., Baldwin, A. S., "TNF-α and cancer therapy-induced apoptosis: Potentiation by inhibition of NF-κB," Science 274: 784-787, 1996). Hence, this mechanism directly connects induction of apoptosis to programmed cell toxicity with inhibition of pro-inflammatory cytokine production and inflammation.

Apoptosis is an essential biochemical process in the body that regulates cells from division (replication) into differentiation and toward an increased functional capacity. Cells entering apoptosis will not only be stimulated to differentiate and increase functionality but will eventually die from this "programmed cell death". Thus, induced apoptosis resulting from NF-κB inhibition by C-MED-100® would (i) effectively kill tumor cells, because they would be forced out of replication by apoptosis and into eventual death; and simultaneously (ii) increase immune cell responsiveness, because more immune competent cells would be forced to differentiate and would live longer because of the parallel enhancement of DNA repair.

NF-κB also sends signals to inflammatory cells instructing them to produce cytokines (growth factors, i.e., TNF-α and the interleukins). These signals, in turn, stimulate phagocytic cells to kill more invading infectious agents, which, at least in part, is accomplished by producing high levels of oxygen free radicals. Thus, inhibiting NF-κB has anti-inflammatory properties because it prevents over-reaction of the inflammatory process that can be harmful to normal body tissues. In addition, because pro-inflammatory cytokines are a major source of endogenous free radical production in humans, NF-κB inhibition is antimutagenic by reducing genetic damage that may accumulate over the years. As fewer radicals are produced, there is less damage to the DNA and less inhibition of natural repair. A result is that aging is curtailed.

It is now shown that quinic acid and its salts, including quinic acid ammonium salt, have an effect on NF-κB in vivo corresponding to the effect of CAEs in vitro.

The Pero extract, preferably C-MED-100® or ACTIVAR AC-11™, is thus an ultimate nutritional supplement for antiaging remedies because it prevents free radical damage by NF-κB inhibition, induces differentiation and immune cell responsiveness by apoptosis, enhances DNA repair, and kills tumor cells, which in turn are the major factors related to aging. (Sheng, Y., Pero, R. W., Amiri, A. and Bryngelsson, C., "Induction of apoptosis and inhibition of proliferation and clonogenic growth of human leukemic cell lines treated with aqueous extracts of *Uncaria Tomentosa*," Anticancer Research 18:3363-3368 (1998); Sandoval-Chacon M., Thompson J. H., Zhang X. J., Liu X., Mannick E. E., Sadowicka H., Charbonet R. M., Clark D. A., Miller M. J., "Anti-inflammatory actions of cat's claw: the role of NF-kappa B," Aliment Pharmacol. Ther. 12: 1279-1289, 1998; Sandoval M., Charbonnet R. M., Okuharna N. N., Roberts J., Krenova Z., Trentacosti A. M., Miller M. J., "Cat's claw inhibits TNF alpha production and scavenges free radicals: role in cytoprotection," Free Radicals Biol. Med. 29(1): 71-78, 2000; Åkesson C., Lindgren H., Pero R. W., Leanderson T., Ivars F., "An extract of *Uncaria Tomentosa* inhibiting cell division and NF-κB activity without inducing cell death," International Immunopharm 3:1889-1900 (2003)). It is beneficial to identify the active component thereof. By isolating and identifying the active component, it is possible to purify the component and enhance the pharmaceutical use and increase the efficacy thereof.

The present invention is directed to the isolation, purification and identification of the CAEs characterized as the active ingredients of the Pero extract in vitro, which CAEs are identified and structurally elucidated as quinic acid analogs. The present invention also is directed to the isolation, purification and identification of quinic acid and quinic acid salts, including quinic acid ammonium salt, as the active ingredients of the Pero extract in vivo. The present invention also is directed to the use of quinic acid and quinic acid salts, including quinic acid ammonium salt, in vivo to enhance immune competency, treat disorders associated with the immune system, inhibit the inflammatory response, treat disorders associated with the inflammatory response, enhance the DNA repair process, enhance the anti-tumor response, and treat disorders associated with the response to tumor formation and growth.

BRIEF SUMMARY OF THE INVENTION

If the plant species *Uncaria* is hot water extracted, which has been the historical practice for medicinal use, and then ultrafiltrated to deplete large molecular weight (>10,000) components, including, for example, toxic conjugates of tannins, there still remains in the non-ultrafiltrated fraction, a novel phytomedicinal preparation of *Uncaria* (e.g. C-MED-100®, ACTIVAR AC-11™) having potent immuno, anti-tumor, anti-inflammatory, and DNA repair enhancing properties. In a preferred embodiment of the present invention, C-MED-100® or ACTIVAR AC-11™ is dissolved in water, spray dried and the spray drying agent (starch) removed by precipitation with 90% aqueous ethanol. The resultant solution is subjected to thin layer chromatography (TLC) on silica gel to identify the active ingredient(s) giving the product its efficacy. The 90% ethanol C-MED-100®/ACTIVAR AC-11™ is spotted on (applied to) TLC plates (silica gel 60 $F_{254}$) and then chromatographed in a system of approximately 1% ammonia in greater than about 95% ethanol. There is only one area on the TLC chromatogram having biological activity (at $R_f$=0.2-0.3) when eluted with 1% aqueous ammonia and subsequently bioassayed for the ability to kill tumor cells by induction of apoptosis. The $R_f$=0.2-0.3 compound shows an ultraviolet absorption maximum in water at about 200 nm, absorbs onto charcoal and is characterized chemically as a CAE by reaction with hydroxylamine and ferric chloride. (Bartos, "Colorimetric determination of organic compounds by formation of hydroxamic acids," Talanta 27: 583-590, 1980).

In another embodiment of this invention, the biologically active CAEs isolated from the Pero extract, preferably C-MED-100®& or ACTIVAR AC-11™, are further purified and structurally identified as a quinic acid analog. Elution from silica TLC plates with aqueous ammonia proved to be necessary because of very tight binding to silica. Although the $R_f$=0.2-0.3 spot is essentially free from other C-MED-100®/ACTIVAR AC-11™ components, it contains relative large amounts of dissolved inorganic silica. In order to remove the inorganic component(s) introduced from the purification scheme on silica TLC, the 1% aqueous ammonia solution is freeze dried and then re-dissolved in methanol, leaving behind the solubilized silica. The $R_f$=0.2-0.3 spot is crystallized from methanol and subsequently identified by chemical analysis as quinic acid.

Thus, one embodiment of the present invention comprises a method for isolating the bioactive component of the Pero extract, preferably C-MED-100® or ACTIVAR AC-11™, comprising: (a) precipitating the spray drying carrier from the Pero extract by mixing the extract with distilled water and evaporating the ethanol, and freeze drying the water-dissolved extract; (b) mixing the freeze-dried extract with distilled water and ethanol to obtain a spotting mixture for thin layer chromatography; (c) spotting the mixture on pre-run TLC plates and chromatographing the plates in a system of approximately 1% ammonia and ethanol, thereby obtaining a fluorescing band with $R_f$=0.2-0.3; (d) scraping off the fluorescing band with $R_f$=0.2-0.3; (e) eluting the scraped band with aqueous ammonia and freeze drying the eluted scraped band to dryness to form a powder; (f) extracting the powder with methanol to remove solubilized silica gel, leaving a methanol solution; (g) concentrating the methanol solution; and (h) crystallizing the concentrated solution to obtain the bioactive component.

Another embodiment of the present invention comprises identification of the in vitro bioactive component of the Pero extract, preferably C-MED-100® or ACTIVAR AC-11™, obtained by the foregoing method. In this embodiment the in vitro bioactive component exhibits the same properties as the Pero extract and consists essentially of a quinic acid analog. Preferably, the quinic acid analog is quinic acid lactone and/or other alkyl esters.

Another embodiment of the present invention comprises identification of the in vivo bioactive component of the Pero extract, preferably C-MED-100® or ACTIVAR AC-11™, obtained by the foregoing method. In this embodiment the in vivo bioactive component exhibits the same properties as the Pero extract and consists essentially of quinic acid and its salts, including quinic acid ammonium salt.

In another embodiment, the present invention comprises a pharmaceutical composition comprising a pharmaceutically effective amount of the bioactive component of the Pero extract and a nontoxic inert carrier or diluent. The present invention also includes embodiments which comprise using the pharmaceutical composition to (i) enhance the immune competency of a mammal by inhibiting TNF-α production or inducing apoptosis of white blood cells, comprising administering the pharmaceutical composition in an amount effective to inhibit TNF-α production or to induce apoptosis of white blood cells; (ii) treat disorders associated with the immune system of a mammal by inhibiting TNF-α production or inducing apoptosis of white blood cells, comprising administering the pharmaceutical composition in an amount effective to inhibit TNF-α production or to induce apoptosis of white blood cells; (iii) inhibit the inflammatory response of a mammal by inhibiting TNF-α production or inducing apoptosis of white blood cells, comprising administering the pharmaceutical composition in an amount effective to inhibit TNF-α production or to induce apoptosis of white blood cells; (iv) treat disorders associated with the inflammatory response of a mammal by inhibiting TNF-α production or inducing apoptosis of white blood cells or increasing white blood cells (WBC) in vivo after chemotherapy-induced leucopenia, comprising administering the pharmaceutical composition in an amount effective to inhibit TNF-α production or to induce apoptosis of white blood cells; (v) enhance the anti-tumor response of a mammal by inducing apoptosis of tumor cells, comprising administering the pharmaceutical composition in an amount effective to induce apoptosis of tumor cells; (vi) treat disorders associated with the response of a mammal to tumor formation and growth by inducing apoptosis of tumor cells, comprising administering the pharmaceutical composition in an amount effective to induce apoptosis of tumor cells; and (vii) enhance the DNA repair processes of a mammal, and, thus, provide anti-mutagenic activity important to treating aging disorders.

BRIEF DESCRIPTION OF THE DRAWINGS

FIG. 3A illustrates Raji cells ($2\times10^5$) that were cultured in the presence of indicated concentrations of C-MED-100®, QAA or QA. Growth rate was assayed after 48 hours by counting triplicate samples of duplicate cultures in a Coulter cell counter. Results from one representative experiment out of two performed is presented as mean values of cell/ml±standard deviation (S.D).

FIG. 3B illustrates triplicate samples of cells from duplicate parallel cultures stained with trypan blue at indicated times and counted. The data show the mean number of viable cells/ml±S.D. from one out of two similar experiments.

FIGS. 3C, 3D and 3E show that C-MED-100®, QAA and QA do not induce cell death. Cells from the same cultures as in FIG. 3B were stained with Annexin V and 7AAD and analyzed by flow cytometry. The results are presented as the mean number of Annexin $V^+$ $7AAD^-$ (apoptotic) or $7AAD^+$ (dead) cells±S.D. of duplicates from three experiments with similar results. Statistically significant differences (*p<0.05) and (**p<0.01), compared to Raji cells grown in medium (no drug).

FIG. 4A illustrates spleen cells ($2\times10^5$) that were activated with Con A (left; 2.5 μg/ml) or LPS (right; 10 μg/ml) in the presence of indicated concentrations of C-MED-100®, QAA or QA. Proliferation was assayed after 48 hours by $^3$[H]-thymidine incorporation in triplicate cultures. Results from one representative experiment out of three are presented as mean values±S.D.

FIGS. 4B and 4C (left panels) show that neither C-MED-100®, QAA nor QA induce cell death. Cells from parallel cultures were stained with trypan blue and the mean absolute number of viable and dead cells/ml from one out of three similar experiments are shown. FIGS. 4B and 4C (right panels) show that C-MED-100®, QAA and QA do not induce apoptosis. Aliquots of the above cultures were stained with Annexin V and 7AAD and analyzed by flow cytometry. The results are presented as the mean number of Annexin $V^+7AAD^-$ (apoptotic) and $7AAD^+$ (dead) cells/ml±S.D. of duplicates from three experiments with similar results. Statistically significant differences (*p<0.05) and (**p<0.01) compared to the control cultures stimulated with Con A (FIG. 4B) or LPS (FIG. 4C) alone.

FIG. 5A illustrates Jurkat T that are cells transfected with a NF-κB reporter construct were pre-cultured with various concentrations of QA or C-MED-100® for two hours. PMA (50 ng/ml) and ionomycin (1 μM) were thereafter added and the cells incubated for another six hours. The mean induction of luciferase activity in triplicate cultures from one representative experiment out of four are shown (left panel). QA induced no cell death or apoptosis in Jurkat T cells at concentrations which inhibited NF-κB activity. Jurkat T cells were incubated with various concentrations of QA for 24 hours and thereafter stained with Annexin V and 7AAD before analysis by flow cytometry. The data are the mean values±S.D. of triplicates from one representative experiment out of two performed (right panel).

FIG. 5B illustrates 70Z/3 cells ($2 \times 10^5$) that were pretreated for 4 h with C-MED-100® or QA before activation for 20 h with LPS (25 μg/ml). The cells were thereafter stained with 7AAD and Igκ-antibodies and analyzed by flow cytometry. The results are mean Igκ-positive cells±S.D. (left panel) and mean 7AAD negative cells±S.D. (right panel) of duplicate cultures from one representative experiment out of two performed.

FIGS. 5C and 5D illustrate 70Z/3 cells ($5 \times 10^6$) that were pre-treated with QA (2 mg/ml) or with PDTC (100 μM) as a positive control for two hours and thereafter stimulated with LPS (25 μg/ml) for the indicated time. Cytoplasmic extracts equalized for protein concentration were analyzed by western blotting using IκBα-specific antibodies. One representative experiment out of three (FIG. 5C) and one representative experiment out of two (FIG. 5D) are presented.

FIGS. 7A and 7B illustrate that the number of WBC, lymphocytes (FIG. 7A) and erythrocytes (RBC) (FIG. 7B) in peripheral blood was determined using an automatic cell counter. The data are presented as the mean number of cells/ml±S.D. from five experiments (water, n=21; C-MED-100® 4 mg/ml, n=24; C-MED-100® 8 mg/ml, n=9; QA 1 mg/ml, n=9; QA 2 mg/ml, n=22; QA 4 mg/ml, n=10). Statistically significant differences compared to control mice supplemented with tap water are indicated.

DETAILED DESCRIPTION OF THE INVENTION

The method and composition of the present invention are best understood with reference to the following examples:

Example 1

Isolation and Purification of the In Vitro Bioactive Component of the Pero Extract The method of preparation and the composition of the Pero extract, preferably C-MED-100® or ACTIVAR AC-11™, are described in the Pero patents which are incorporated herein by reference. C-MED-100® and ACTIVAR AC-11™, preferred embodiments of the Pero extract, are hot water extractions of Cat's Claw (*Uncaria tomentosa*) carried out for 18-24 hours at 90-100° C. and ultra-filtrated to remove compounds greater than 10,000 molecular weight as previously described in the Pero patents. C-MED-100® is further prepared for the commercial market by spray drying the extract with corn starch (Niro F-10 Spray-Drier). Procedures are currently used to purify the in vitro active components of C-MED-100® as CAEs and it is understood that these procedures would apply to any Pero extract. The procedures are:

1. C-MED-100® work-up for active ingredient estimation: The CAEs in C-MED-100® have very unusual water solubility. They tend to bind to tannin and polysaccharide polymers, and so, when dried, are difficult to redissolve in appropriate organic solvents such as ethanol. The preferred procedure, and it should be understood that the parameters provided are approximations and not strict limitations, is:

(a) 100 mg of C-MED-100® is dissolved in 1 ml distilled water in a glass tube for 30 minutes. The dissolved solution is centrifuged at 2000×g for 10 minutes. The resulting first supernatant is reserved for analysis.

(b) 200 μl of the first supernatant is placed into a new glass tube, and 4.8 ml of 99.7% ethanol is added thereto. The resulting solution contains 4 mg/ml C-MED-100® suspended in about 96% ethanol.

(c) The C-MED-100®/ethanol solution is vortexed (mixed) and centrifuged at 2000×g to remove insoluble material. The resulting second supernatant is reserved for analysis.

(d) The second supernatant is diluted from a C-MED-100® concentration of 4 mg/ml to one of 30-200 μg/ml with 99.7% ethanol for measurement of UV absorbence. Preferably, concentrations of 60 and 120 μg/ml are examined as duplicate concentrations for calculation of CAE by UV absorbence.

Figure 1:
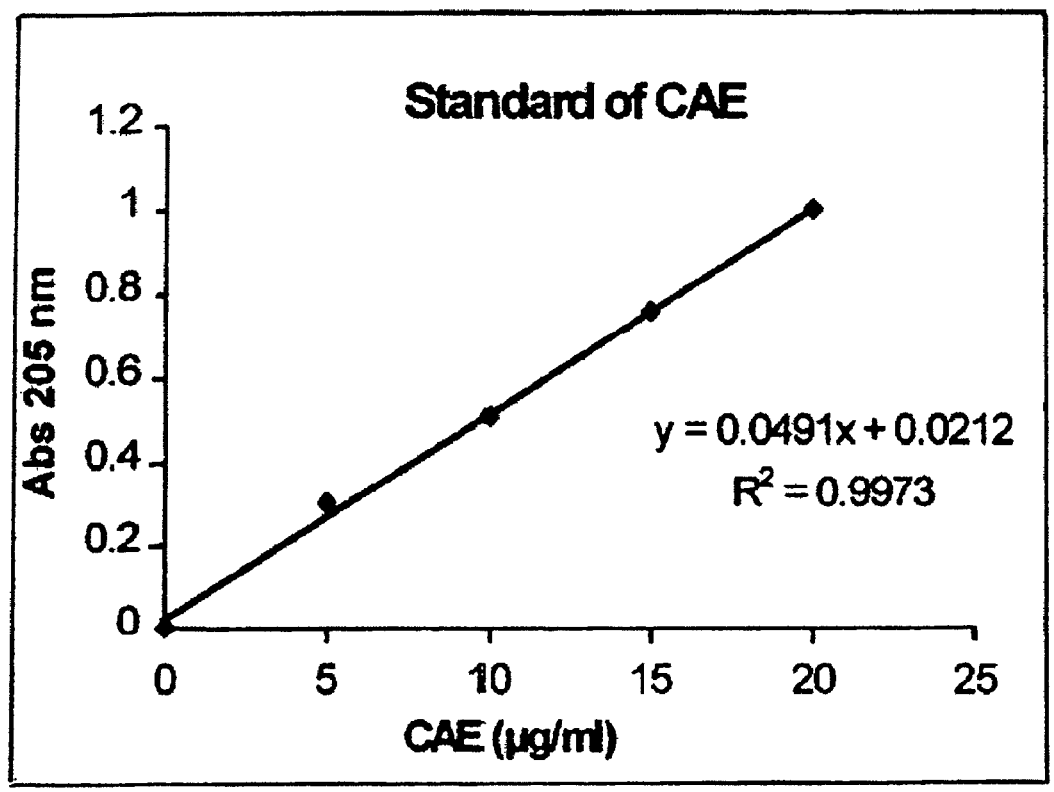
FIG. 1 shows the linear regression of UV absorbence versus CAE (estimated as _g/ml using dioctyl phthalate as standard).

(e) The UV absorbence at 205 nm for the two concentrations of C-MED-100® (preferably 60 and 120 μg/ml) is measured in a UV spectrophotometer. Because the CAEs in C-MED-100® have a UV maximum absorption at 205 nm, the amount of CAE may be estimated by the degree of UV absorption. The standard curve showing the amount of CAE in μg/ml in relation to the degree of UV absorption is shown in FIG. 1.

(f) Calculation of the concentration of CAEs, in μg/ml, is determined by linear regression analysis of the slope of best fit by the equation y=0.0491x+0.212, where y=UV absorbence values determined and x=concentration of CAE (μg/ml). The two different concentrations of C-MED-100® (preferably 60 and 120 μg/ml) then serve as the denominator for which the calculated CAE from the UV standard curve serves as the nominator in the calculation of percentage CAE in C-MED-100®. In practice, the two values are averaged.

(g) The foregoing procedure has been validated against a colorimetric procedure involving conversion of CAE to hydroxamic acids and reaction with ferric chloride. (Bartos, Colorimetric determination of organic compounds by formation of hydroxamic acids, Telanta 27: 583-590, 1980). The two procedures give the same estimation of CAE content.

2. Analytical procedures for final purification and isolation of C-MED-100®'s active ingredient. Again, the parameters provided are approximations and should serve as exemplary not as limitations:

(i) Precipitation of spray drying carrier (corn starch) from crude water extracts of C-MED-100®: 5 g of C-MED-100® is mixed with 50 ml distilled water and 950 ml 99.7% ethanol. The ethanol is evaporated off in the air and the resulting solution is freeze dried. Yield is approximately 1 g.

(ii) Silica gel thin layer chromatography (TLC) purification and isolation of C-MED-100®'s active ingredient:

Step 1: To 200 mg C-MED-100® minus the removal of starch (after procedure no. 1 above), add 200 μl distilled water and 200 μl 95.5% ethanol. Mix to form a spotting mixture.

Step 2: Spot the spotting mixture of Step 1 on 4 pre-run TLC plates (Silica gel 60F$_{254}$). The elution system consists of approximately 1% NH$_3$ in at least 95% ethanol. The sole active component is found at R$_f$=0.2-0.3.

Step 3: Scrape off the fluorescing blue band with R$_f$=0.2-0.3. Eluate with approximately 1% aqueous ammonia and freeze dry to dryness.

Step 4: Extract the powder from Step 3 with methanol to remove solubilized silica gel. Concentrate the methanol solution and crystallize the active component.

(iii) High pressure liquid chromatography (HPLC) quantitative determination of active component: The column preferably is a 3 μm C$_{18}$ column (83 mm×4.3 mm internal diameter, Perkin Elmer Corp., Norwalk, Conn.). The preferred solvent gradient elution is as follows: Pump B contains methanol and pump A contains 1% acetic acid in distilled water. A gradient was run from 10% to 90% over a period of 25 minutes at a flow rate at 1.5 ml/min. Detection is at UV 254 nm. The peak appears at 18 minutes into the gradient run.

(iv) Spectrophotometric detection of active ingredients: The active component of C-MED-100® has an absorption maximum in water in the UV range at about 200 nm. Hence, crude extracts of C-MED-100® also having an absorption maximum at about 200 nm as well as its purified active components such as CAEs and their corresponding organic acids can be estimated by UV absorption at this wavelength against a known CAE standard.

An assay of biological activity of C-MED-100®'s active ingredient is prepared as follows: HL-60 W6899 cells are exposed in microculture at 5000 cells per well (96-well plates) for 5 days at 37° C. in a CO$_2$ incubator. After incubation, the cells are washed with saline and clonogenicity estimated by MTT assay. Results of the assay are summarized in Table 1, below.

Example 2

Analytical Identification of the Active Ingredient of C-MED-100® as Quinic Acid

The bioactive component (sample approximately 1 mg) isolated by TLC is completely dissolved in about 0.7 ml D$_2$O for NMR with no shift reagent added. The following spectra are recorded:

NMR 020108ta
1: $^1$H
2: $^1$H/$^1$H-correlated spectra; COSY
3: $^1$H/$^{13}$C-correlated spectra; HMBC.
4: $^{13}$C-Dept135.
5: $^1$H/$^{13}$C-correlated spectra; HMQ The $^1$H-spectrum contains signals from a main compound. The three $^1$H-signals at 4.03, 3.90 and 3.43 ppm are found to be signals from methine-groups (see HMQC). Furthermore, the obtained $^{13}$C-signals at 66.9 B 75.1 correlate to these protons, and their chemical shifts imply that the carbons are bound to oxygen, possibly as CHOH-groups. The three signals are bound to each other in a straight chain as found in the COSY spectrum.

The main compound also showed $^1$H-signals at about 1.72 B 1.99 ppm with correlations to $^{13}$C-signals at about 40 ppm. The HMQC spectrum reveals that these signals are CH$_2$-groups and the COSY spectrum implies that the individual protons in each CH$_2$-group are unequal.

Judged from the COSY spectrum, the two outer CHOH-groups are bound to different CH$_2$-groups. This gives the following partial structure:

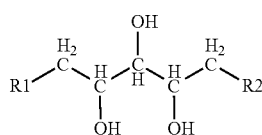

However, as many of the $^1$H-$^1$H-couplings were larger/smaller compared with normal couplings it seemed likely that the compound rotation was sterically hindered and therefore a ring system was suggested. Furthermore, as the $^{13}$C-shifts for the CH$_2$-groups were near 40 ppm it seemed likely that R1=R2=a carbon atom. This gave the following partial structure:

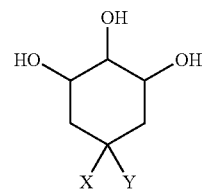

No signals that explain X and Y in the compound could be found in the NMR spectra. After the NMR spectra were obtained also MS-analysis was performed. The sample was introduced into the MS by infusion. MS spectra on the D$_2$O solution diluted with acetonitrile (ACN) (50/50) gave the mass number of 197 (negative ions, M-D=195). Then the solution was evaporated by means of a gentle stream of nitrogen and reconstituted in H$_2$O/ACN (50/50). Here the mass number 192 was achieved (negative ions, M-H=191). In conclusion, the compound mass number is 192 and contains 5 exchangeable protons. When combining the information obtained from NMR and MS the following structure is proposed for the main compound:

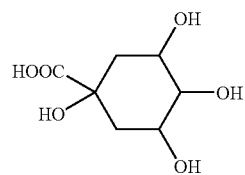

Quinic Acid

This structure is quinic acid. Reference spectra obtained using authentic quinic acid were identical to that isolated and purified from C-MED-100®.

Quinic acid, now identified as the active ingredient of C-MED-100®, is a known compound occurring as an intermediate metabolite in the natural synthesis of many aromatic compounds. (Bohm, B A, Shikimic acid (3,4,5-trihydroxy-1-cyclohexene-1-carboxylic acid), Chem. Rev. 65: 435-466, 1965). Hence, it is disclosed here that quinic acid and its analogs are expected to occur in many botanical species, giving them added nutritional and health benefits.

The only known prior art disclosing any medical uses of quinic acid and its analogs is for the treatment of skin wrinkles (U.S. Pat. Nos. 5,656,665 and 5,589,505) and of flu as neuroamidase inhibitors (U.S. Pat. Nos. 6,111,132 and 6,225,341). There has been no prior art disclosure that quinic acid and its analogs might be useful in treating the disorders for which C-MED-100® has been useful such as aging, inflammation, immune suppression, and control of tumor growth and DNA repair.

Hence, this disclosure is of these additional uses for quinic acid and its analogs, especially quinic acid lactone. Moreover, quinic acid does not give a positive chemical reaction for a CAE. However, upon review of this structure, it became apparent that quinic acid might form a quinic acid lactone upon heating, which in turn would react as a CAE. (Fischer, H. O. and Dangschat, G. Helv. Chim Acta 18: 1200, 1935). Furthermore, treating the quinic acid lactone with 1% aqueous ammonia could convert it back to quinic acid. This chemistry was validated using purified quinic acid, and establishes that the active ingredient present in C-MED-100® has been synthesized during the historical medical preparation of this Cat's Claw product.

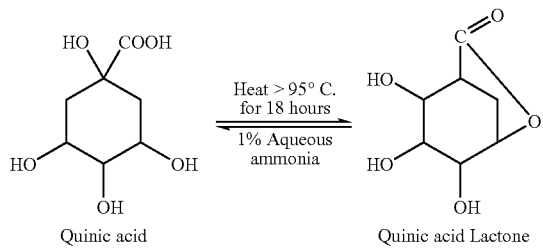

Example 3 provides this validation.

Example 3

This Example exploits the biochemical knowledge presented in examples 1 and 2 to determine that the active component of C-MED-100® in vitro is in fact quinic acid lactone. C-MED-100®, quinic acid and quinic acid lactone all absorb to charcoal, and when they did both the biological activity and UV absorption at 200 nm of C-MED-100® was also removed. This data teaches that the bioactive component of C-MED-100® absorbs maximally at 200 nm. The TLC results report that there are only 2 components of C-MED-100® having such an absorption maxima. The components, located at $R_f=0.1$ and $R_f=0.3$, when chromatographed in 1% ammonia in ethanol, correspond to quinic acid and quinic acid lactone, respectively.

However, upon evaluation, the in vitro bioactive properties of the bioactive component of C-MED-100® could be almost completely accounted for by quinic acid lactone. As a result, the in vitro anti-aging, anti-inflammatory, immune and DNA repair enhancing and anti-tumor properties of C-MED-100® are due to the presence of quinic acid lactone and other relevant quinic acid alkyl esters. Those properties are hereby disclosed as attributable to quinic acid lactone.

Table 1 illustrates the relative biochemical activities of (i) the isolated in vitro bioactive component of C-MED-100®, (ii) quinic acid, and (iii) quinic acid lactone:

TABLE 1

Comparison of active ingredient of C-MED-100 ® to quinic acid and its lactone.

| Chemical Parameter | C-MED-100 ® active ingredient | Quinic acid | Quinic acid lactone |
|---|---|---|---|
| Charcoal absorption in water | Yes | yes | yes |
| $A_{UV}$ maximum in water | 200 nm | 200 nm | 200 nm |
| TLC in approximately 1% ammonia in 99% ethanol using $A_{200}$ nm for detection | $R_f = 0-0.1$ $R_f = 0.2-0.3$ | $R_f = 0-0.05$ | $R_f = 0.2-0.3$ |
| Formation of hydroxamic acid/ferric chloride color complex | Yes | no | yes |
| Bioassay efficacy using $IC_{50}$ in HL-60 cells | 40 µg/ml | >3000 µg/ml | 80 µg/ml |
| Bioassay after 1% aqueous ammonia $IC_{50}$ HL-60 cells | >3000 µg/ml | >3000 µg/ml | >3000 µg/ml |

(Parameters are approximations.)

From the foregoing comparison, it is apparent that the in vitro bioactive component in C-MED-100® is, in fact, quinic acid lactone. Specifically, the relative $IC_{50}$ values for the in vitro C-MED-100® bioactive component, quinic acid, and quinic acid lactone confirm that the in vitro bioactive component cannot be quinic acid, per se, but must be an analog thereof, such as quinic acid lactone. The difference in $IC_{50}$ values for the in vitro C-MED-100® bioactive component and quinic acid lactone is not significant, and is likely due to the synergistic effect of other compounds present in C-MED-100®. However, the higher efficacy of the active ingredient, quinic acid lactone, in C-MED-100® than in its pure form indicates that the quinic acid lactone is more active in the presence of other naturally occurring components in C-MED-100® such as quinic acid.

It has recently been determined that quinic acid, while not the principal bioactive ingredient of C-MED-100® in vitro, is in fact the principal bioactive ingredient of that compound in vivo. It has also been determined that quinic acid salts, including quinic acid ammonium salt, also are bioactive components of C-MED-100® and ACTIVAR AC-11™ in vivo.

Example 4

Presented below in Table 2 teaches that quinic acid analogs could exist in C-MED-100® and ACTIVAR AC-11™ in 3 possible forms: (i) as a free acid, (ii) as a salt; e.g. sodium salt or ammonium salt, or (iii) as an ester such as quinic acid lactone, and any one of the 3 forms or combinations thereof could explain the biological efficacy of C-MED-100®. For example, if quinic acid is present as a salt it can have in vitro biological activity comparable to C-MED-100®. However, Table 2 also teaches that because C-MED-100® is very sensitive to base hydrolysis, the major component of C-MED-100® that is efficacious in vitro must be the quinic acid esters since, when quinic acid ester content disappears, so does the in vitro biological activity, and these changes are accompanied by an increased content of quinic acid. It is also taught in Table 2 that C-MED-100® contains not only quinic acid esters but also significant amounts of quinic acid itself before any base hydrolysis, supporting that at least two active forms of quinic acid analogs in C-MED-100® exist together and could possibly synergize each other. Even this principle of quinic acid/quinic acid lactone synergism is disclosed in Table 2 because a synthesized batch of quinic acid lactone containing 5% impurity of quinic acid, had much greater cytotoxicity than a 99% batch of quinic acid lactone. In summation, Example 4 teaches that although the primary in vitro bioactive ingredients in C-MED-100® are quinic acid esters such as quinic acid lactone or yet unidentified quinic acid alkyl esters, because other quinic acid equivalents are present such as free acid quinic acid or its salts that could synergize or otherwise explain the biological efficacy of C-MED-100®, they should also be considered bioactive forms of quinic acid.

TABLE 2

Quinic acid (QA) (free acid), quinic acid salts and quinic acid esters; i.e., quinic acid lactone (QAL) analyzed as bioactive ingredients of C-MED-100 ®, that is in turn shown to be coupled to the simultaneous disappearance of in vitro biological efficacy and quinic acid ester content.

| Compound | HL-60 MTT $IC_{50}$ (μg/ml) | % QA esters (Bartos) | QA est. by TLC |
|---|---|---|---|
| Quinic acid (QA) sodium salt | 1500 | 0 | ++++ |
| QA ammonium salt | 500 | 0 | ++++ |
| QA (free acid) (>99% pure, Sigma) | >2300 | 0 | ++++ |
| QAL #1 batch syn. (+5% QA impurity) | 1200 | >91% | not detected |
| QAL #2 batch syn. (>99% pure) | >2300 | 100% | 0 |
| QAL (>99%) (+2 M NaOH, 2 hr) | 1600 | 35% | ++ |
| C-MED-100 ® (no base hydrolysis) | 536 | 4.7% | + |
| C-MED-100 ® (+2 M NaOH for 2 hr) | 1100 | 2.5% | ++ |

In Table 2, the in vitro cytotoxicity of the various components were determined in HL-60 human leukemic cells using the MTT assay and calculation of $IC_{50}$ values as described in detail elsewhere. Quinic acid ester content was determined by the Bartos method (Bartos, 1980). Quinic acid content was estimated by thin layer chromatography (TLC) on silica gel 60 $F_{254}$ plates developed in a system of 1% ammonia in 95.5% ethanol. The quinic acid traveling between $R_f$=0.2-0.3 was eluted from the TLC plates with 1% aqueous ammonia and the relative quantity estimated by absorption at 200 nm as ± being less than 0.050 and "++++" denoting the highest amount detected, with a decrease in the number of "+" signs corresponding to a decrease in the amount of QA detected.

Example 5

Further extends and verifies the information already presented in Example 4. Because oral administration of C-MED-100® would necessitate gastrointestinal (GI) tract absorption of its active ingredients, there exists the possibility that the forms of quinic acid equivalents found in C-MED-100® would all be metabolized to quinic acid in vivo, no matter the quinic acid structure they were administered in. For example, the pH of the stomach is about 1 and this condition is strong enough to hydrolyze quinic acid esters, including quinic acid lactone, to quinic acid. Furthermore, the GI tract is rich in non-specific esterases that could also hydrolyze quinic acid esters to quinic acid. Likewise the intestinal microflora have a very active Shikimate pathway which can utilize quinic acid equivalents to synthesize chlorogenic acid and a host of other bioactive components (Herrmann K M, Weaver L M. The Shikimate Pathway. Annu Rev Plant Physiol Plant Mol Biol 1999; 50: 473-503). For these reasons, the free acid form of quinic acid and the ammonium salt form thereof were tested for in vivo efficacy using a rat model that had been already used successfully with C-MED-100® to treat chemotherapy-induced leucopenia tin the rat (Sheng Y, Pero R W, Wagner H. Treatment of chemotherapy-induced leukopenia in a rat model with aqueous extract from Uncaria tomentosa. Phytomedicine 2000; 7: 137-43).

In vivo evaluation of the efficacy of quinic acid as an active ingredient isolated from water soluble Cat's Claw extracts. A rat model was used to evaluate if active ingredients isolated from water soluble extracts of Cat's Claw could be shown to be effective in vivo by inducing recovery of peripheral white blood cells (WBC) after doxorubicin (DXR)-induced leucopenia. This model has already been used effectively to demonstrate C-MED-100® administration after DXR treatment enhanced recovery of WBC about as efficiently as NEUPOGEN®, a standard therapy used in the clinic for this purpose (Sheng et al. Phytomedicine 2000; 7: 137-43). The rat study experimental design used to compare quinic acid and C-MED-100® is outlined in detail (diagrammatic form) below.

50 female W/Fu rats, weighing 150-180 g each, were divided into 5 groups of 10 rats per group. Doxorubicin, obtained from Pharmacia and Upjohn, was administered in a 2 mg/kg dose for all rats groups 2-5, IP injection (day 1, 3, 5). Group 3 also received C-MED-100® (Batch No E-40622), administered in a dose of 80 mg/kg, gavage daily from day 6 (24 hours after the third/last treatment of DXR) to the end of experiment (day 21/22). Group 4 received Quinic acid (QA, obtained from Sigma), administered at a dose of 200 mg/kg, gavage as per C-MED-100®t. Group 5 received ammonia-treated quinic acid (QAA), synthesized by neutralizing QA with 1% ammonia and then lypholyzing to dryness, and administered at 200 mg/kg, gavage as C-MED-100®. The supplemental drug (gavage) for each of the groups of test rats is set forth in the below table:

| 1 | Group | 2 | No. | 3 | Doxorubicin (I.P.) | 4 | Supplement drug (gavage) |
|---|---|---|---|---|---|---|---|
| 5 | 1. Control | 6 | 10 | 7 | Saline Control | 8 | Sterile tap water gavage |
| 9 | 2. Doxorubicin (DXR) | 10 | 10 | 11 | 2 mg/kg × 3 | 12 | Sterile tap water gavage |
| 13 | 3. C-MED-100 ® (80 mg/kg) | 14 | 10 | 15 | 2 mg/kg × 3 | 16 | C-MED-100 ® gavage |
| 17 | 4. DXR + QA (200 mg/kg) | 18 | 10 | 19 | 2 mg/kg × 3 | 20 | QA (200 mg/kg) gavage |
| 21 | 5. DXR + QAA (200 mg/kg) | 22 | 10 | 23 | 2 mg/kg × 3 | 24 | QA-ammonium (200 mg/kg) gavage |

The body weight (GM) of each rat was measured before and at the end of the experiment. Blood was sampled on day 0 (before any treatment), day 4 (24 hours after the second DXR treatment), day 7 (48 hours after the third/last DXR treatment), day 11, and day 15. Whole peripheral blood samples were collected into $K_3$-EDTA containing tubes by periorbital puncture and then analyzed for WBC within 1 hour with an automated hematology analyzer (Sysmex, K-1000) Organ weights from major tissues (liver, kidney, lung, heart, spleen) were also collected and used as an indicator of any toxicity.

Identification of quinic acid (QA) as an active ingredient of water extracts of Cat's Claw; e.g. C-MED-100®, ACTIVAR AC-11™. The characterization, isolation and final purification of the bioactive component in Cat's claw water extracts by silica gel TLC has been described herein. We have obtained additional chemical and biological evidence that demonstrates that the in vivo bioactive ingredient in C-MED-100® or ACTIVAR AC-11™ is quinic acid (QA). First, the only area on the TLC plates chromatographed in 1% ammonia in 95% ethanol that had biological activity assessed by the HL-60 bioassay was at $R_f$=0.2-0.3. As the 1 cm scraped TLC plate sections were eluted from the silica gel with 1% ammonia, any acids or esters present at this $R_f$ location would have been converted to an ammonium salt, and this analog would have had the biological activity attributed to C-MED-100®. Nevertheless, the ammonia eluant was freeze dried, re-dissolved in water and the UV spectrum determined to have an absorption maximum at 200 nm.

It is understood that research presented herein demonstrating the biological activity and biologically active component(s) of C-MED-100® is applicable, as well, to ACTIVAR AC-11™, as both products contain the Pero extract, merely in different levels of CAEs.

Figure 2:
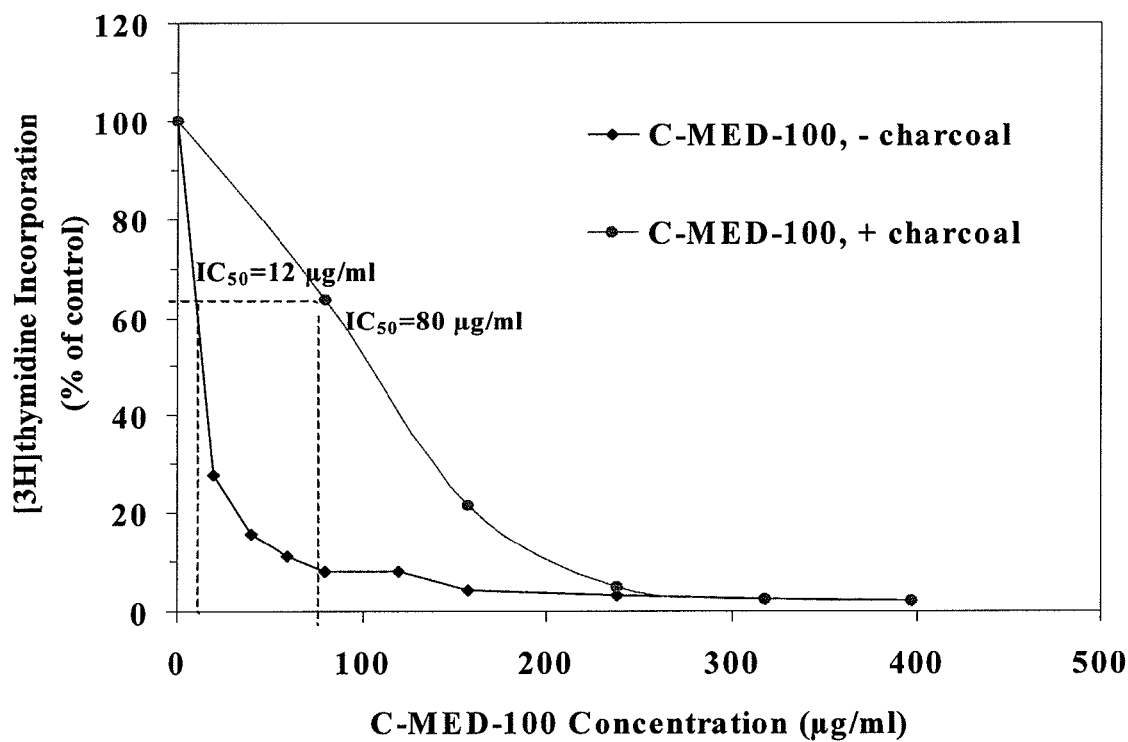
FIG. 2 shows the influence of UV absorbing compounds removed by charcoal adsorption on the $^3$[H] thymidine incorporation of HL-60 cells in vitro.

Because of the possibility of base hydrolysis of esters or ammonium salt/chelate formation of acids of the bioactive component, the UV absorption maximum of C-MED-100® dissolved in water but not treated with ammonia was determined. C-MED-100® also had an UV absorption maximum of 200 nm in water or ethanol. These data led to the conclusion that removing the UV absorbing material from C-MED-100® would also remove the biological activity. For this purpose, a comparison of C-MED-100® water solutions before and after activated charcoal absorption (1 gm/1 ml C-MED-100®/gm charcoal) was carried out. The data from such an experiment are presented in FIG. 2, which shows that >85% of the in vitro HL-60 cytotoxicity in C-MED-100® extract was removed due to charcoal absorption, and likewise it was paralleled by removal of >85% 200 nm UV absorbing materials. Since the only 200 nm UV absorbing components in C-MED-100® were located at $R_f$=0.2-0.3, and since C-MED-100® had a 200 nm UV absorption maximum which if removed by charcoal absorption also destroyed its biological activity, the active ingredient of C-MED-100® can only be attributed to components absorbing at 200 nm and traveling on silica gel 60 $F_{254}$ TLC plates chromatographed in 1% ammonia in 95% ethanol to $R_f$=0.2-0.3.

The C-MED-100® component at $R_f$=0.2-0.3 was crystallized from methanol and subjected to analytical chemical analysis. NMR analyses indicated the $^1$H-spectrum contained signals from a main compound. The three $^1$H-signals at 4.03, 3.90 and 3.43 ppm were found to be signals from methine-groups from HMQC- and Department reference 135—experiments spectra. Furthermore, the obtained $^{13}$C-signals at 66.9-75.1 correlated to these protons and their chemical shifts imply that the carbons are bound to oxygen, possibly as CHOH— groups. The three $^1$H-signals are also bound to each other in a straight chain as found in the COSY spectrum. The C-MED-100® compound also showed $^1$H-signals at about 1.72-1.99 ppm with correlations to $^{13}$C-signals at about 40 ppm. The reference 135 spectrum revealed that these signals were $CH_2$-groups and the COSY spectrum implied that the individual protons in each $CH_2$-group were unequal.

Judged from the COSY spectrum the two outer CHOH-groups were bound two different $CH_2$-groups and this suggested a straight chain structure. However, as many of the $^1$H-$^1$H-couplings were larger/smaller compared with normal couplings it seemed likely that the compound rotation had steric hindrance and therefore a ring system was suggested. Furthermore, as the $^{13}$C-shifts for the $CH_2$-groups were near 40 ppm it seemed likely two carbon atoms were outside the ring structure.

After the NMR spectra were obtained MS-analysis was also performed. MS spectra on the $D_2O$ solution diluted with acetonitrile (ACN) (50/50) gave the mass number of 197 (negative ions, M-D=195). Then the solution was evaporated by means of a gentle stream of nitrogen and reconstituted in $H_2O$/ACN (50/50). Here the mass number 192 was achieved (negative ions, M-H=191). In conclusion, the C-MED-100® in vivo bioactive compound had a mass number is 192 and contained 5 exchangeable protons. After combining the information obtained from NMR and MS the structure of QA was proposed for the C-MED-100® active compound in vivo.

Quantitative determination and in vitro biological evaluation of QA analogs in water extracts of Cat's claw; e.g. C-MED-100®, ACTIVAR AC-11™. As QA has been found to be an active ingredient in C-MED-100® and ACTIVAR AC-11™ in vivo, and in light of the uncertainty that QA may have arisen as a result of base hydrolysis elution from silica gel after TLC, we have attempted to determine the presence of potential QA analogs in C-MED-100®. For this purpose, we have developed 3 chemical procedures that are capable of estimating various types of QA analogs that might be present in C-MED-100®, namely: (i) CAEs by UV absorption at 200 nm quantified against dioctyl phalthalate; (ii) QA esters using quinic acid lactone (QAL) as the standard ester and quantified by the Bartos reaction by forming hydroxamic acids and chromaphores with ferric chloride; and (iii) by NaOH neutralization that in turn estimates any free acid equivalents present in C-MED-100®. Data for these analyses are presented in Table 3, indicating about 8-10% CAE esters (w/w) present in C-MED-100®, of which 4-5% could be accounted for as QA esters. In addition, <1.6% (w/w) of C-MED-100® existed as the free QA analog (H+ form). We concluded that either free QA existed as an active ingredient in C-MED-100® at <1.6%, or there was a QA ester analog which had a free non-esterified carboxyl group present. In either case, these data are consistent with the major active ingredients in C-MED-100® in vitro as being CAEs in the form of QA esters.

To further characterize the QA analogs as the active ingredients in C-MED-100® in vitro, we determined the influence of base hydrolysis on the chemistry and biological activity of C-MED-100®. QAL is in fact a cyclic ester of QA, and as such it is an example representing the general class of QA esters. Elution from silica gel with 1% ammonia were the mandated chemical conditions necessary to remove the QA analog (i.e., active ingredient) from silica gel, which in turn favored the base hydrolysis of QA esters such as QAL to QA. If so, then identification of QA after base hydrolysis from the elution of silica gel, would then be consistent with the natural occurrence in C-MED-100® of a QA ester at $R_f$=0.2-0.3. Hence, it was undertaken to prove that QAL as an example of QA esters was indeed hydrolyzed by either 1N HCl or 1M NaOH. The data are presented in Table 3. It is quite clear that either strong acid or base treatment converted QAL to QA, and left only QA remaining, thus supporting the fact that the isolation of QA from C-MED-100® after base elution from silica gel was likely to have been originally present as a QA ester.

TABLE 3

The acid and base hydrolysis of QAL and QA. The disappearance of the ester linkage in QAL was measured by formation of hydroxamic acids and colormetric development with ferric chloride using the Bartos reaction. The lack of breakdown of QA was also confirmed by TLC and UV absorption at 200 nm.

| Compound | µg/test | Bartos Reaction ($A_{490}$ nm) | | | |
|---|---|---|---|---|---|
| | | Initial | Average | -Blank | % Degraded |
| Blank | 0 | 0.175 | 0.175 | 0 | — |
| QA | 500 | 0.170 | | ±0 | ±0 |
| QA | 500 | 0.172 | 0.172 | | |
| QAL | 500 | 0.742 | | | |
| | 500 | 0.752 | 0.747 | 0.572 | |
| QAL (1N HCl) | 500 | 0.413 | | 0.238 | 58.2% |
| QAL (1M NaOH) | 500 | 0.323 | 0.368 | 0.1920 | 74.1% |
| QA (1N HCl) | 500 | 0.170 | 0.176 | | |
| QA (1M NaOH) | 500 | 0.175 | 0.169 | ±0 | ±0 |

Having confirmed that base hydrolysis converted QA acid esters to QA, we proceeded to quantify C-MED-100® for the presence of certain types QA analogs. The data in Table 4 utilize 3 separate chemical procedures to estimate the relative amounts of potential QA analogs found in unhydrolyzed C-MED-100®. First of all there is maximally <1.6% QA in C-MED-100, because by base neutralization there were only a total of <1.6% free acid equivalents which also included all other acids that might have been present, and thus contributing to the acidity of C-MED-100®. Hence QA alone cannot account for the in vitro efficacy of C-MED-100®. However, there was a much more substantial amount of CAEs, and this class of compounds had already been shown to contribute to the efficacy of C-MED-100® (FIG. 1), and at least about 4-5% of the CAEs could be accounted for as QA esters (Table 4).

TABLE 4 i The average content of QA analogs in C-MED-100 ®.

| C-MED-100 ® Batch number | UV $A_{200\,nm}$ Method (dioctyl phthalate std.)) CAE est. % w/w | Bartos Method (QAL ester std.) QA ester est. % w/w | pH Method (NaOH neut.) Free acid est. % w/w |
|---|---|---|---|
| E-42526 | 9.0 | 4.6 | <1.6 |
| E-43183 | 9.8 | 4.8 | <1.7 |
| E-43229 | 9.4 | 4.6 | <1.8 |
| E-43682 | 9.4 | 4.8 | <1.4 |
| E-43751 | 9.2 | 4.7 | <1.9 |
| E-44038 | 8.8 | 4.4 | <1.6 |
| E-44073 | 8.8 | 4.7 | <1.9 |
| Average | 9.2 | 4.7 | <1.7 |

In vivo efficacy studies of QA in the rat. There are two physiological factors regarding the natural forms of QA as the active ingredients of water extracts of Cat's Claw such as C-MED-100® or ACTIVAR AC-11™ which, in turn, might result in quite different biological responses when administered in vitro or in vivo. Firstly, there was the pH=1 of the stomach that we have shown is strong enough to hydrolyze any QA esters present in C-MED-100® to QA (Tables 3 and 5). Secondly, the microflora of the digestive tract of mammals are well known to both synthesize and metabolically convert QA to other analogs such as chlorogenic acid, ferrulic acid, shikimic acid, cinnamonic acid, and benzoic acid (Seifter E, et al. 1971. Nutritional response to feeding L-phenylacetic, shikimic and D-quinic acids in weanling rats. J Nutr 101(6): 747-54; Gonthier M P, et al. 2003. Chlorogenic acid bioavailability largely depends on its metabolism by the gut microflora in rats. J Nutr 133(6): 1853-63). These well known physiologic facts have raised the possibility that even though QA esters are the bioactive ingredients in vitro, QA esters in vivo could have been metabolized to QA before being absorbed into circulation to mediate efficacious responses. In order to test the hypothesis that natural occurring QA esters identified in C-MED-100® might be catabolized to QA in vivo and yet still be bioactive, we have directly compared the efficacy of QA and QAA to C-MED-100® in a rat model. This in vivo model discloses that DXR-induced leucopenia is restored to normal WBC levels about as efficiently as standard therapy for this purpose, i.e. NEUPOGEN®, after receiving oral daily doses of C-MED-100® for 14 days of 40-80 mg/kg (Sheng et al. 2000. Phytomed 7(2): 137-143). Table 5 displays the data of rats given 3 doses of DXR (2 mg/kg) on days 1, 3, and 5 after initiation of the experiment, and then followed by oral daily administration of either water (control), C-MED-100®, QA or QAA for 6-21 days thereafter. Peripheral blood WBC were recorded throughout this time period, and the data indicated both QA or QAA could induce recovery from DXR-induced leucopenia about as effectively as 80 mg/kg C-MED-100® could. Furthermore, weight loss and organ pathology did not indicate any toxicity for the doses of C-MED-100® or its active ingredients that were tested. Based on these data we conclude that a QA analog is at least one class of active ingredients also observed for water soluble Cat's Claw water extracts, e.g. C-MED-100®, ACTIVAR AC-11™.

TABLE 5

Enhanced recovery of doxorubucin (DXR) induced-leucopenia in the rat by treatment with C-MED-100 ® or quinic acid (QA).

| Group* | n | Treatment and sampling schedule ($10^{12}$ WBC/l) | | | | |
|---|---|---|---|---|---|---|
| | | Day 0 | Day 4 | Day 7 | Day 11 | Day 15 |
| Control (saline, gavage) | 10 | 9.5 ± 1.4 | 8.8 ± 0.9 | 9. ± 1.0 | 9.2 ± 1.1 | 9.0 ± 0.8** |
| DXR (2 mg/kg, ip) | 10 | 9.5 ± 1.4 | 5.9 ± 0.7 | 5.3 ± 0.7 | 6.2 ± 0.7 | 7.1 ± 1.0 |

TABLE 5-continued

Enhanced recovery of doxorubucin (DXR) induced-leucopenia in the rat by treatment with C-MED-100 ® or quinic acid (QA).

| Group* | n | Treatment and sampling schedule ($10^{12}$ WBC/l) | | | | |
|---|---|---|---|---|---|---|
| | | Day 0 | Day 4 | Day 7 | Day 11 | Day 15 |
| C-MED-100 ® (80 mg/kg, gavage) | 10 | 9.6 ± 1.4 | 5.4 ± 0.7 | 5.7 ± 1.1 | 7.6 ± 1.7 | 8.4 ± 1.5** |
| QA (200 mg/kg, gavage) | 10 | 9.5 ± 1.5 | 6.5 ± 1.1 | 5.5 ± 0.9 | 6.4 ± 0.7 | 8.1 ± 1.5** |
| QAA (200 mg/kg, gavage | 10 | 9.5 ± 1.1 | 6.5 ± 0.9 | 5.2 ± 0.5 | 6.7 ± 1.1 | 8.5 ± 1.0** |

*DXR treatment days were 1, 3, and 5 followed by C-MED-100 ®, QA or QAA treatment for 6-11 days thereafter
**= $p < 0.05$ compared to DXR alone, all other groups were not significantly different after 15 days of treatment.

The data presented in Table 5 clearly teach that both QA and QAA were about as effective as 100 mg/kg of C-MED-100® at reversing doxorubicin-induced leucopenia. Because this in vivo model has been successfully used previously to demonstrate the broad range of clinical indications attributed to C-MED-100® and other cat's claw water extracts, such as recovery from chemotherapy-induced leucopenia, DNA repair enhancement, anti-inflammation, immune stimulation, anti-tumor effects and anti-aging effects including Alzheimer's and cognitive reasoning, there is little doubt that QA equivalents including not only QA esters but QA itself and its salts, including QAA, are active ingredients of C-MED-100® (in vivo.

Example 6

We further identify QA as a biologically active component of the Pero extract in vivo, and demonstrate that QA increases splenic leukocyte numbers in vivo and inhibits NF-κB activity in cells grown in tissue culture in vitro.

Materials and Methods: C57BL/6 females were bought from M&B A/S, Ry, Denmark and used in experiments at an age of 6-10 weeks. The animals were kept in a SPF facility at Lund University, Lund, Sweden. The use of laboratory animals complies with the guidelines of the European Community and was approved of by the local ethical committee.

C-MED-100® was supplied by CampaMed, Inc. (New York, N.Y.), recently acquired by Optigenex, Inc (New York, N.Y.). Quinic acid (1,3,4,5-tetrahydroxy-cyclohexanecarboxylic acid) (QA) was bought from Sigma-Aldrich (Stockholm, Sweden). Both C-MED-100® and QA were dissolved in RPMI medium 30 minutes before use in in vitro cultures. QA was isolated from C-MED-100® (as already described in detail elsewhere (WO 2003/074062 and Sheng Y, et al. An active ingredient of Cat's Claw water extracts. Identification and efficacy of quinic acid. Jour Ethnopharmacology In Press, 2004). Briefly, C-MED-100® was subjected to TLC chromatography in 1% ammonia in ethanol, eluted from the TLC plates in 1% ammonia in water and crystallized from methanol after neutralization and acidification with HCl.

In vivo treatment: Mice were fed with C-MED-100® and QA (Sigma-Aldrich), dissolved in autoclaved tap water at indicated concentrations, for 21 days. The drinking water bottles were changed every third day. The animals were then sacrificed, the spleens removed and blood samples collected. The blood samples were analyzed in a Sysmex KX-21N cytometer (Sysmex Corporation, Kobe, Japan).

Fluorochrome-conjugated reagents: Fluorescein isothiocyanate (FITC)-conjugated anti-CD8α (YTS169.4), anti-CD4 (GK1.5), anti-B220 (RA3.6B2), anti-Igκ and Cyanin 5 (Cy-5)-conjugated anti-B220 (RA3.6B2) were prepared in our laboratory. Phycoerythrine (PE)-conjugated anti-CD4 (RM4-5) and anti-CD8α (53-6.7) and allophycocyanin (APC)-conjugated TCRβ (H57-597) were bought from BD Biosciences (San Diego, Calif.). 7-amino-actinomycin D (7AAD) was bought from Sigma-Aldrich. Annexin V-FITC was bought from Molecular Probes (Leiden, Holland).

Flow cytometry: Cells were counted and aliquots of $10^6$ cells were stained with monoclonal antibodies in FACS-buffer (HBSS supplemented with 0.1% ($NaN_3$) and 3% fetal calf serum (FCS) (Life Technologies, Paisley, GB), as previously described (Åkesson C, et al. C-Med 100, a hot water extract of *Uncaria Tomentosa*, prolongs lymphocyte survival in vivo. Phytomedicine 10: 23-33 (2003)). Spleen cells were pre-incubated for 10 min on ice with the anti-Fc-receptor antibody 2.4G2 (FcγRIII/II) (prepared in our laboratory) to prevent non-specific binding to Fc-receptors. The cells were analysed with a FACSCalibur flow cytometer (Becton Dickinson, San Jose, Calif.).

Cell cultures: Raji human Burkitt's lymphoma (CCL-86), Jurkat human acute T-cell leukemia (TIB-152), 70Z/3 mouse pre-B lymphocyte cell line (TIB-158), or mouse spleen cells were used in the experiments. The cells were cultured in RPMI medium (Life Technologies) supplemented with 10% FCS, 10 mM HEPES buffer, antibiotics, 50 µM 2-mercaptoethanol and 1 mM sodium pyruvate (all supplements from Life Technologies) at 37° C., 5% CO2. The number of Raji cells in duplicate cultures were determined with a Coulter Z1 cell counter (Beckman Coulter Inc, Fullerton, Calif., USA) three times each. The number of viable and dead cells were determined using trypan blue exclusion, by counting three independent samples from duplicate cultures. Cells were stained with 2 µg/ml 7-amino-actinomycin D (7AAD; Sigma-Aldrich, St Louis, Mo., USA) and with Annexin V (Molecular Probes) according to the manufacturer's protocol and the cells were defined as apoptotic (Annexin V+7AAD⁻) or dead (7AAD⁺) by flow cytometry. Spleen cells were polyclonally activated with 2.5 µg/ml concanavalin A (Con A; Amersham Pharmacia, Uppsala, Sweden) or 10 µg/ml lipopolysaccharide (LPS; Sigma-Aldrich). PMA (50 ng/ml) and ionomycin (1 µM) (both from Sigma-Aldrich) and pyrollidine dithiocarbamate (PDTC) (100 µM, EMD Bioscience Inc, Calbiochem, San Diego, Calif., USA) were used in some cultures as indicated. Proliferation was detected by measuring thymidine incorporation after a 4 hours pulse with 1 µCi $^3$[H]-thymidine (Amersham Pharmacia).

Transient transfection and analysis of luciferase activity: The reporter construct containing NF-κB binding sequences and the luciferase reporter gene was previously described. (Parra E, et al. Costimulation by B7-1 and LFA-3 targets distinct nuclear factors that bind to the interleukin-2 promoter: B7-1 negatively regulates LFA-3-induced NF-AT DNA binding. Mol Cell Biol 17: 1314-23 (1997)). Jurkat T cells were transiently transfected with the construct using the lipofectin method as described by the manufacturer (Life Technologies). After transfection, the cells were rested for 22 hours, pooled and pre-cultured for 2 hours in the presence or absence of C-MED-100® or QA before stimulation. After 6 hours of stimulation, the cells were harvested and washed twice in phosphate-buffered saline (PBS). The cells were lysed and aliquots of the lysates analyzed for luciferase activity using the Luciferase Assay System (Promega, Madison, Wis.). Luminiscence was quantitated in a MicroLumat LB 96 P luminometer (EG&G Berthold, Wallac Sverige A B, Upplands Väsby, Sweden).

Preparation of cell extracts: The 70Z/3 cells were pretreated with QA (1 or 2 mg/ml) or with PDTC for 2 hours before they were stimulated with LPS for various time points. Whole cell extracts from the 70Z/3 cells ($1 \times 10^6$) were prepared for analysis of the NF-κB signaling pathway. The cells were washed twice in PBS, resuspended in lysis buffer (75 mM Tris-HCl (pH 8.0), 100 mM NaCl, 5 mM KCl, 3 mM $MgCl_2$, 2% NP-40, 1 mM PMSF and a protease inhibitor cocktail) (Roche Diagnostics Scandinavia AB) and incubated on ice for 10 min. The cell debris was pelleted and the supernatants were stored at −70° C. until Western Blot was performed.

Western blotting: Cellular extracts from 70Z/3 cells were separated on a 10% SDS polyacrylamide gel and the proteins were transferred to a nylon membrane. After blocking overnight in 5% dry fat-free milk in TBST, the membrane was incubated for 2 hrs with primary antibodies specific either to IκBα or to phosphorylated IκBα (both from Cell Signaling Technology Inc, Beverly, Mass.). The membranes were thereafter washed three times in TBST, and incubated with HRP-conjugated goat anti-rabbit antibodies (Amersham Pharmacia). The membranes were washed three times and chemoluminescence was detected using the ECL-reagent (Amersham Pharmacia) and x-ray film (CEA AB, Strängnäs, Sweden).

Statistics: Statistical analysis was performed using Student's two tailed t-test for unequal variance.

A biologically active component of C-MED-100® in vivo: A biologically active component of C-MED-100® in vivo was isolated as described. The eluted material from one fraction was found to inhibit proliferation of HL-60 cells similarly to the C-MED-100® extract itself. A component in this biologically active fraction was identified by MALDI mass spectrometry as quinic acid (QA), as described in detail elsewhere (Sheng Y, et al. An active ingredient of Cat's Claw water extracts. Identification and efficacy of quinic acid. Submitted for publication). Commercially available QA was used in an effort to confirm this as well as other known biological activities of the of C-MED-100® extract.

Figure 3A:
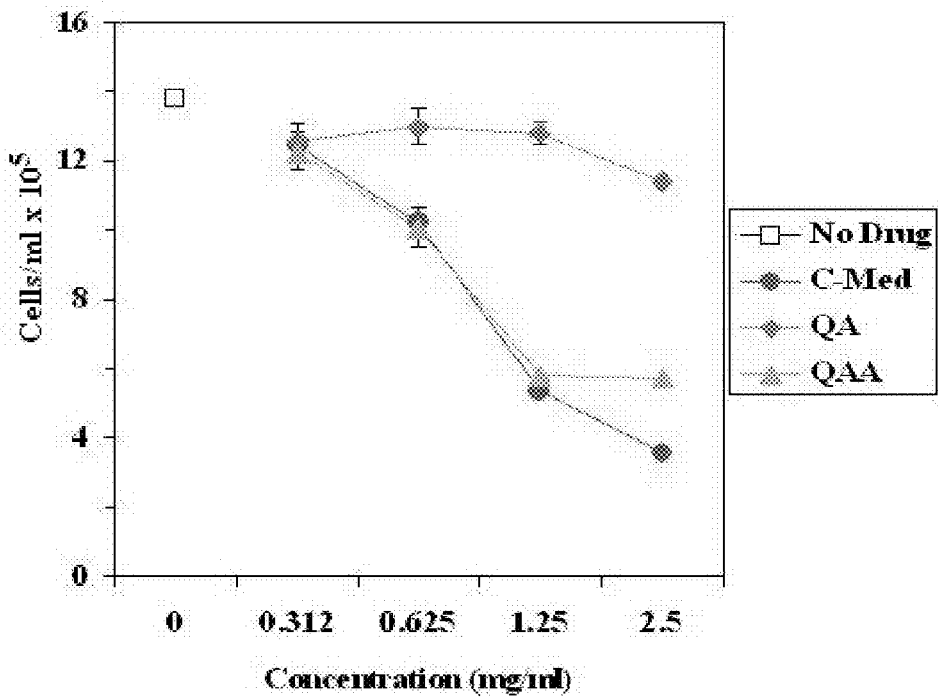
FIGS. 3A-E show that quinic acid treated with ammonia (QAA), but not quinic acid (QA), inhibits Raji cell proliferation.
Figure 3B:
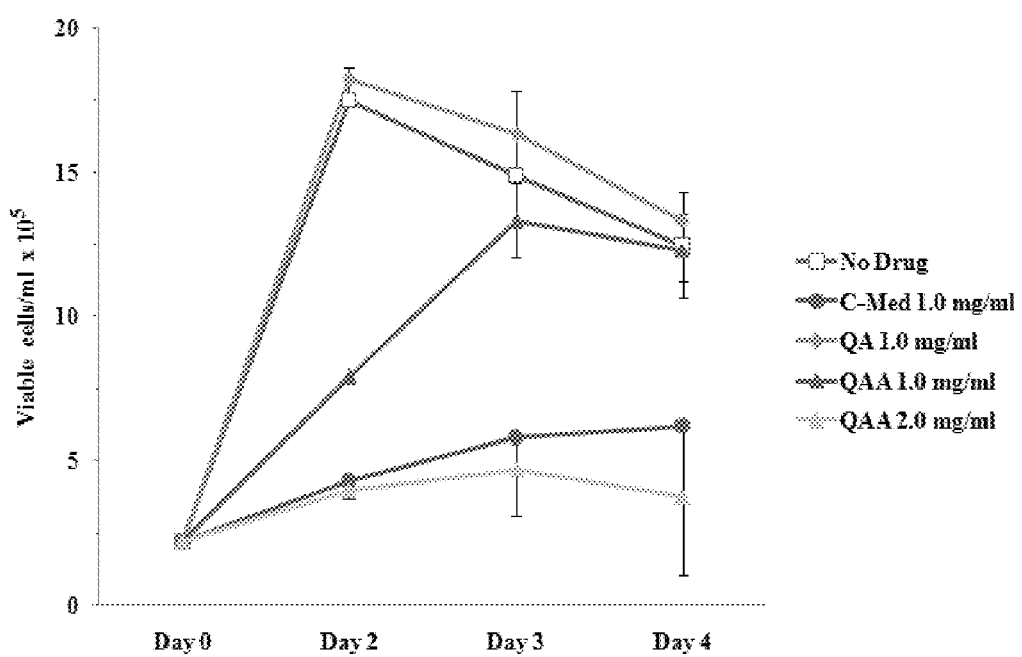
Figure 3C:
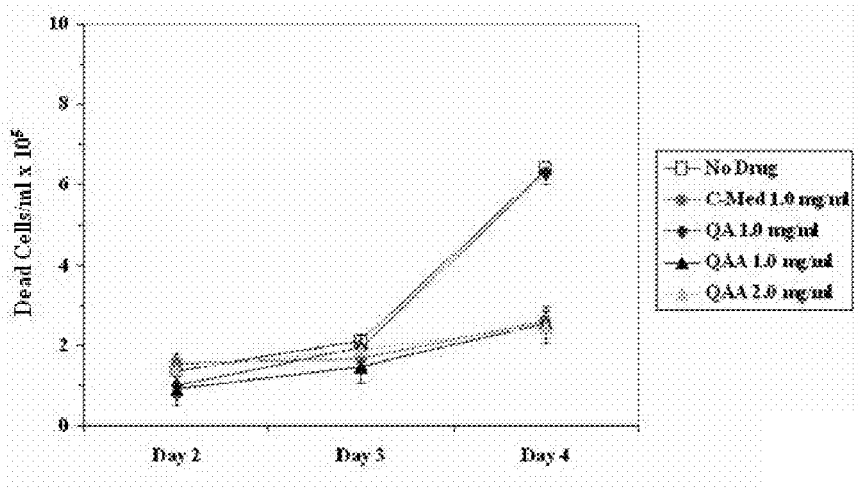
Figure 3D:
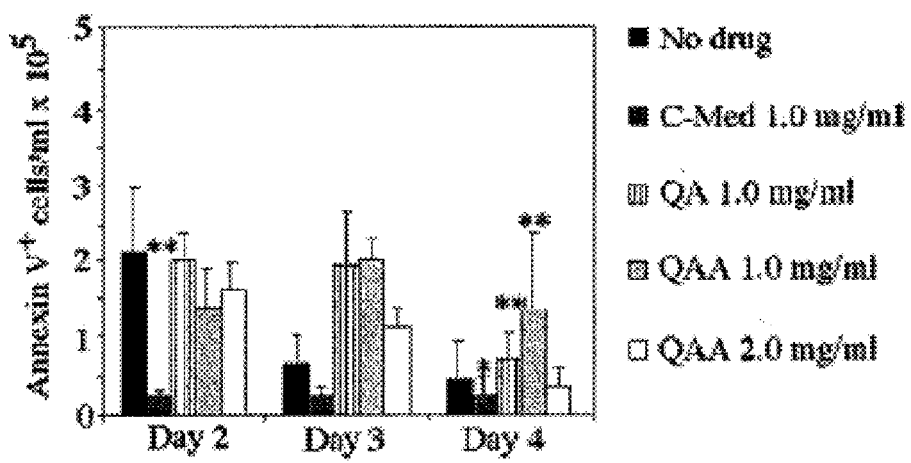
Figure 3E:
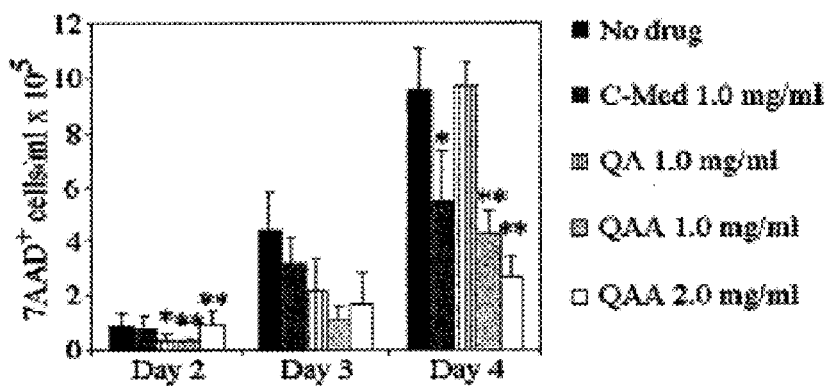
Figure 4A:
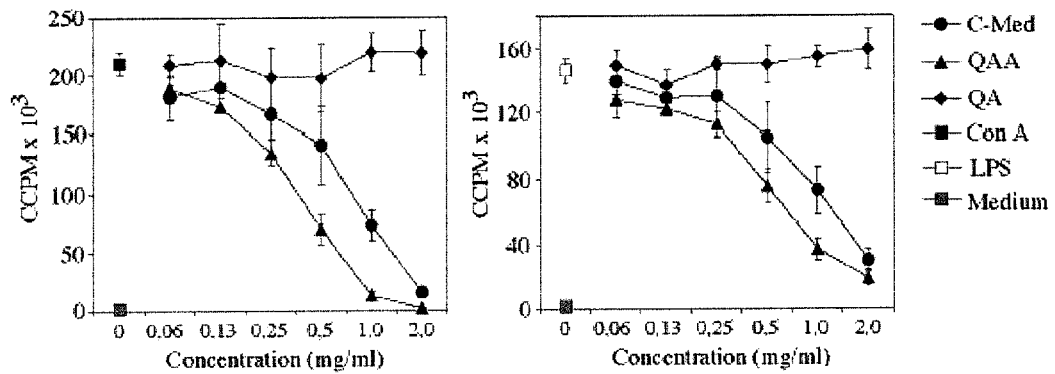
FIGS. 4A-C show that QAA, but not QA, inhibit proliferation of mitogen-stimulated mouse lymphocytes.
Figure 4B:
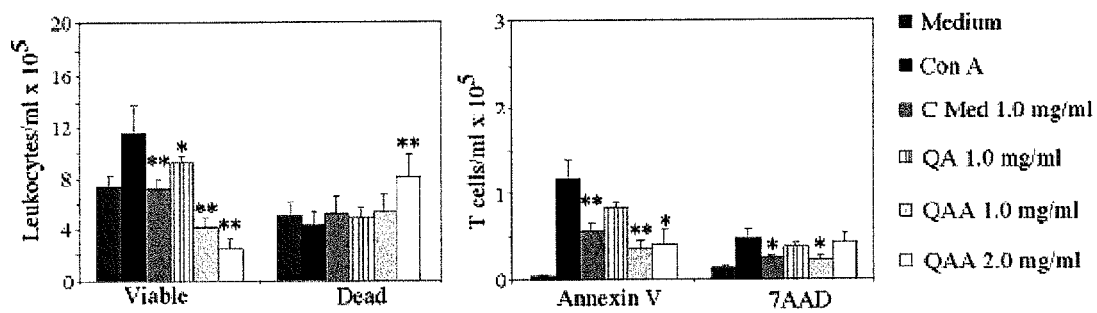
Figure 4C:
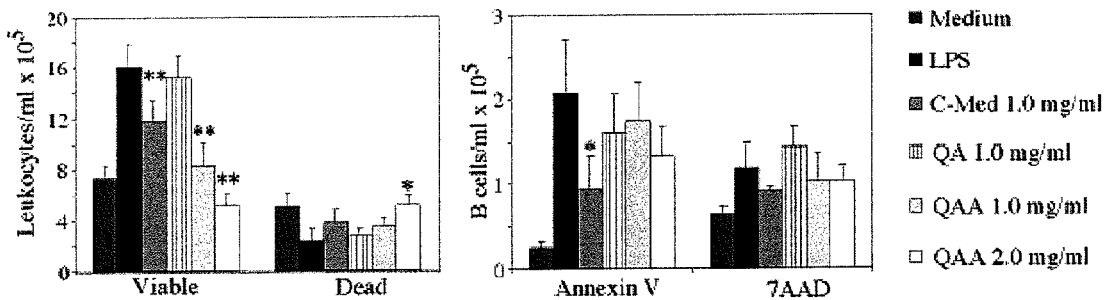

As shown in FIGS. 3A, 3B and 4A, commercially available QA neither inhibited the proliferation of Raji tumor cells nor proliferation of ex vivo murine lymphocytes. One possible explanation for the functional discrepancy between commercial QA and the QA isolated from C-MED-100® might relate to the fact that QA isolated from C-MED-100® was treated with ammonia during chromatography and elution on silica gel. To test this possibility, commercially available QA was treated with 1% ammonia, under identical conditions to those used to isolate QA from C-MED-100® using TLC, and then analyzed its biological activity compared to commercial QA. As expected, ammonia-treated QA (QAA) inhibited cell proliferation in a dose dependent manner (FIGS. 3A, 3B, FIG. 4A) without being overtly toxic (FIG. 3D and FIGS. 4B, 4C). As previously reported (Åkesson C, et al. An extract of Uncaria tomentosa inhibiting cell division and NF-kappaB activity without inducing cell death. Int Immunopharmacol 3: 1889-900 (2003)) and confirmed here, C-MED-100® consistently reduced the fraction of apoptotic cells both in cultures of tumor cells (FIG. 3C) and normal lymphocytes (FIGS. 4B and 4C). QAA also significantly reduced the fraction of apoptotic T cells, while there was a tendency to reduction (p=0.053) in parallel cultures treated with QA (FIG. 4B). This effect was not seen in Raji cells (FIG. 3C) nor in normal B cells (FIG. 4C), 70Z/3 cells or Jurkat T cells (data not shown). This discrepancy remains a focus of future research.

QA inhibits NF-κB activity: It is known that extracts of Uncaria tomentosa inhibit NF-κB activity in cells cultured in vitro. (Åkesson C, et al. Int Immunopharmacol 3: 1889-900 (2003); Aguilar J L, et al. Anti-inflammatory activity of two different extracts of Uncaria tomentosa (Rubiaceae). J Ethnopharmacol 81: 271-6 (2002); Tak P P, Firestein G S. NF-kappaB: a key role in inflammatory diseases. J Clin Invest 107: 7-11 (2001)). To determine whether QA might inhibit this transcriptional regulator, we used Jurkat T cells transfected with a NF-κB dependent reporter gene. The results in FIG. 3A (left) demonstrate that QA, in a dose dependent manner, inhibited the NF-κB activity induced by activating the Jurkat T cells with PMA and ionomycin. The inhibition was observed at concentrations of QA that did not induce cell death (FIG. 3A, right). As would be expected from the data presented above, parallel experiments confirmed that QA did not inhibit proliferation of the Jurkat T cells either (data not shown). Thus, QA inhibits NF-κB activity, without inhibiting proliferation either of normal cells or of tumor cells. QAA inhibited the NF-κB activity to a similar extent as QA (data not shown).

Figure 5A:
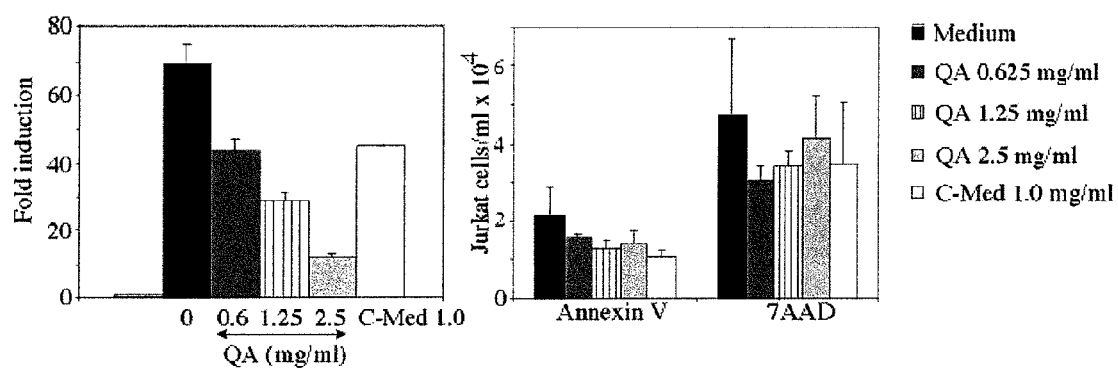
FIGS. 5A-D show C-MED-100® and QA inhibit NF-κB activity.
Figure 5B:
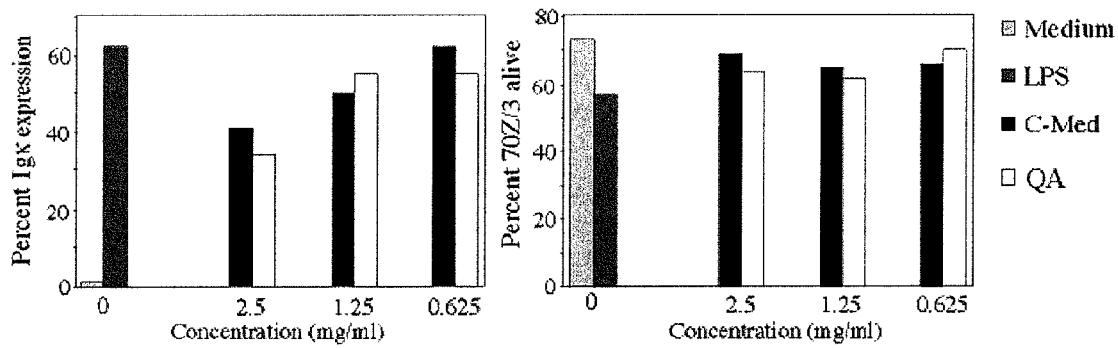
Figure 5C:
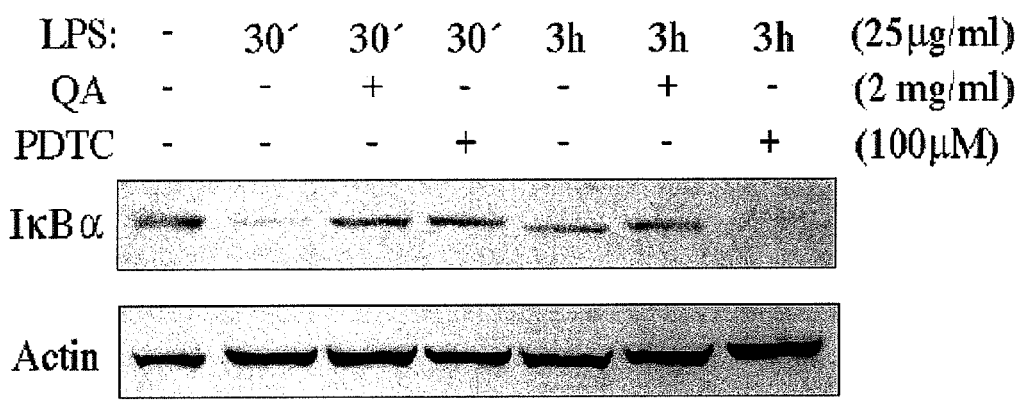
Figure 5D:
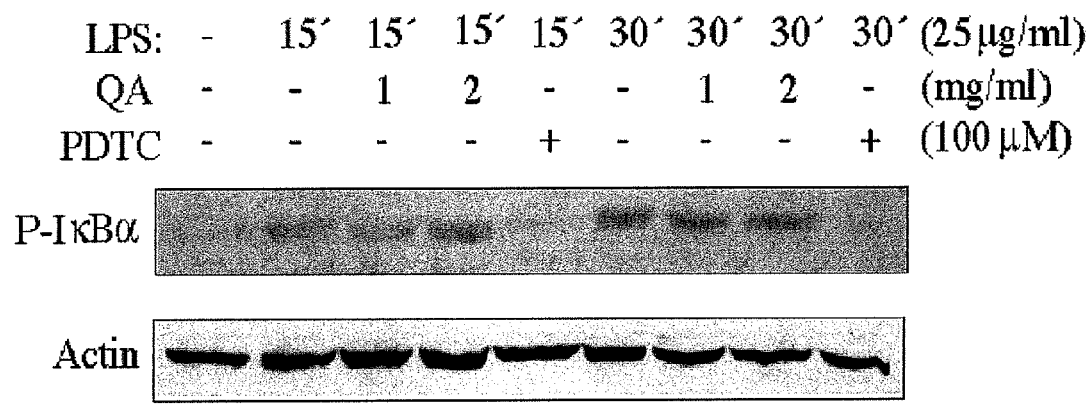

It is known that the LPS-induced Igκ-chain expression in 70Z/3 cells is NF-κB dependent. (Sen R, Baltimore D. Inducibility of kappa immunoglobulin enhancer-binding protein Nf-kappa B by a posttranslational mechanism. Cell 47: 921-8 (1986)). As shown in FIG. 5B, QA and C-MED-100® inhibited Igκ-chain expression to a similar extent (left) without causing cell death (right). This model was used to further explore the mechanism of NF-κB inhibition. As can be seen in FIGS. 5C and 5A, QA inhibited the LPS-induced breakdown of IκBα in these cells, suggesting a plausible mechanism for the inhibition of NF-κB dependent reporter gene transcription. It is known that the antioxidant pyrollidine dithiocarbamate (PDTC) inhibits both the breakdown of IκBα and its resynthesis. (Schreck R, et al. Dithiocarbamates as potent inhibitors of nuclear factor kappa B activation in intact cells. J Exp Med 175: 1181-94 (1992)). Our results confirm this. However, QA did not affect the phosphorylation of IκBα, which in contrast was potently inhibited by PDTC, as shown in FIG. 3D. The QA-induced inhibition of IκBα breakdown is thus controlled at another level than IκBα phosphorylation. We have not further investigated the exact level at which QA inhibits the NF-κB activity.

Increased spleen cell number in QA treated animals: It has been shown that in vivo treatment of mice for three weeks with the C-MED-100® extract increased the number of spleen cells, due to the prolongation of lymphocyte half life. (Åkesson C, et al. Phytomedicine 10: 23-33 (2003)). As shown in FIG. 4A, that observation is confirmed here, using the previously determined optimal concentration of C-MED-100® (4 mg/ml in the drinking water). The observation that a higher concentration of the extract (8 mg/ml) did not increase splenic lymphocyte numbers further, together with previously reported data, demonstrates that this biological effect is only seen in a narrow concentration range. Mice fed with drinking water containing 4 mg/ml C-MED-100® also had significantly higher spleen weight. However, neither of the groups fed with C-MED-100® had significant changes in body weight.

Figure 6A:
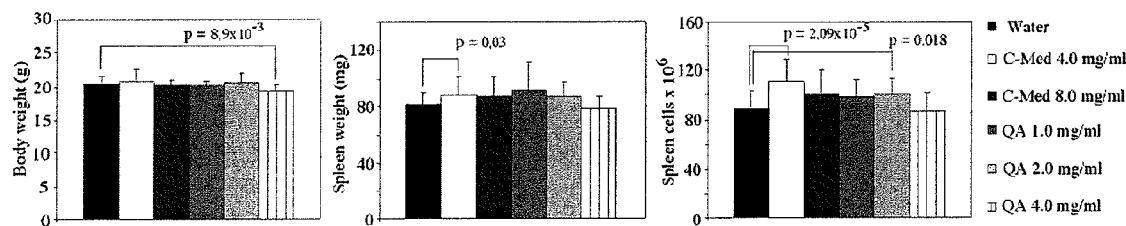
FIGS. 6A-B shows an increased spleen cell number in QA and C-MED-100® treated mice. Mice were treated with indicated concentrations of QA or C-MED-100® in the drinking water for 21 days, sacrificed and absolute number of spleen cells counted using trypan blue exclusion. The presented data are mean cell numbers±S.D. pooled from five experiments (water, n=21; C-MED-100® 4 mg/ml, n=24; C-MED-100® 8 mg/ml, n=9; QA 1 mg/ml, n=9; QA 2 mg/ml, n=22; QA 4 mg/ml, n=10). Statistically significant differences compared to control mice supplemented with tap water are indicated.
Figure 6B:
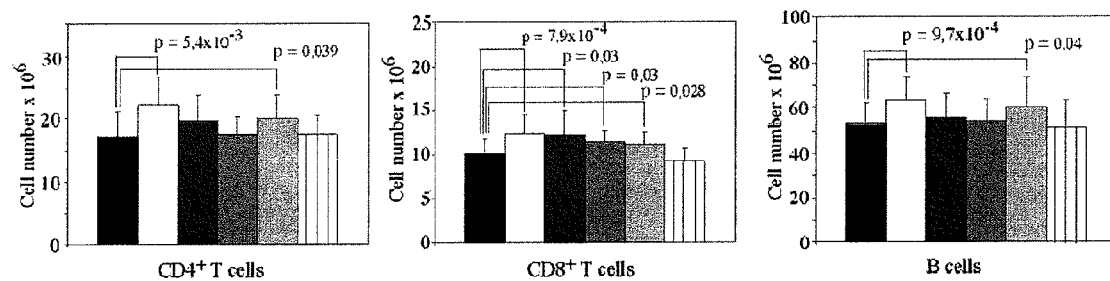

Since QA decreased NF-κB activity in treated cells in vitro, we investigated whether this component might also be involved in the above in vivo biological response. To address this possibility, mice were fed with drinking water containing various concentrations of QA. As shown in FIG. 6A, mice fed with 2 mg/ml of QA had a significantly increased number of spleen cells, but similarly to what was observed in C-MED-100® treated mice, the increase was seen only in a narrow concentration range. It has been shown, and is confirmed here, that the increased spleen cell number was paralleled by significantly increased absolute numbers of the major lymphocyte subsets CD4$^+$ T cells, CD8$^+$ T cells and B cells (Åkesson C, et al. Phytomedicine 10: 23-33 (2003)) (FIG. 6B). Importantly, this was also the case in the QA treated animals. Taken together, these data strongly indicate QA as one candidate compound of this in vivo biological effect of C-MED-100®.

Figure 7A:
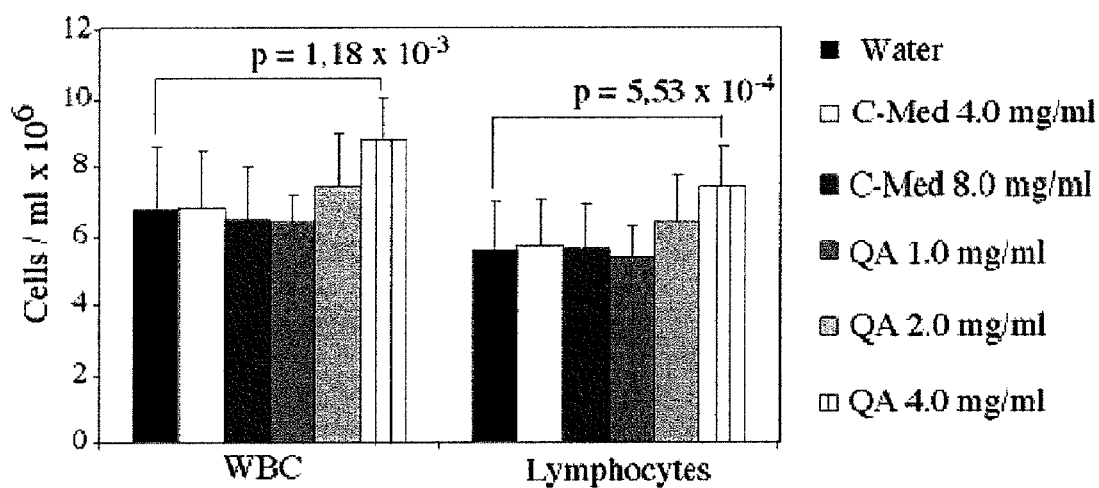
FIGS. 7A-B show an increased number of white blood cells (WBC) in QA treated mice. Mice were treated with indicated concentrations of either QA or C-MED-100® in the drinking water for 21 days and thereafter sacrificed.
Figure 7B:
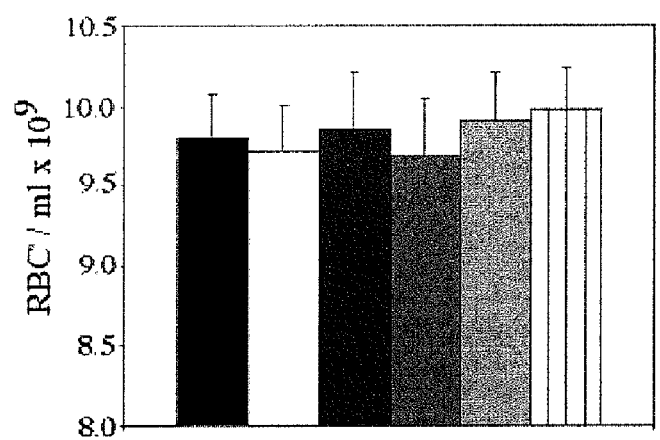

Turning to FIGS. 7A-B, despite the significant increase in spleen cell number, there was no increase in WBC, blood lymphocytes or red blood cells (RBC) observed in C-MED-100® treated mice. In contrast, mice treated with increasing concentrations of QA had increasing number of WBC and blood lymphocytes. In the group treated with 4 mg/ml of QA this increase was significant as compared to normal control animals. However, the body weight of those animals was also significantly reduced so the significance of this observation is difficult to evaluate.

As previously reported (Åkesson C, et al. Int Immunopharmacol 3: 1889-900 (2003)) and confirmed in here, exposure to C-MED-100® also had a significant anti-apoptotic effect on spleen cells at concentrations inhibiting proliferation. However, the number of apoptotic cells was not reduced in cultures exposed to QA or QAA, suggesting that other components of the extract might be responsible for this effect.

It is known that extracts of *Uncaria tomentosa* inhibit the activity of the transcriptional regulator NF-κB (Sandoval-Chacon M, Thompson J H, Zhang X J, Liu X, Mannick E E, et al. Antiinflammatory actions of cat's claw: the role of NF-kappaB. Aliment Pharmacol Ther 12: 1279-89 (1998); Aguilar J L, et al. J Ethnopharmacol 81: 271-6 (2002)). This is most probably one of the reasons for the anti-inflammatory properties of such extracts. (Sandoval M, et al. Cat's claw inhibits TNFalpha production and scavenges free radicals: role in cytoprotection. Free Radic Biol Med 2000; 29: 71-8). It has been shown that the C-MED-100® extract also inhibited NF-κB activity, but without inhibiting degradation or expression of IκBα. (Åkesson C, et al. Int Immunopharmacol 3: 1889-900 (2003)). The data presented here indicate that QA, in a dose-dependent fashion, inhibited the expression of a NF-κB dependent reporter gene in tissue culture cells. A similar level of inhibition was seen using similar concentrations of QAA (data not shown). However, in contrast to the C-MED-100® extract, QA inhibited the degradation of IκBα. These data collectively suggest that QA and C-MED-100® inhibited NF-κB activity by different mechanisms. Further, QA exposure did not detectably interfere with the phosphorylation of IκBα while it inhibited the degradation of that protein, suggesting that QA-induced inhibition of NF-κB activity is regulated at another level. It may seem paradoxical that QA, which is a potent inhibitor of LPS-induced NF-κB activity in 70Z/3 cells, does not inhibit LPS-induced proliferation of normal B cells. However, the toll-like receptor 4 (TLR4)-mediated induction of the MAP-kinase pathway (reviewed in O'Neill L A. Signal transduction pathways activated by the IL-1 receptor/toll-like receptor superfamily. Curr Top Microbiol Immunol 2002; 270: 47-61) may still occur in these cells and be sufficient to induce proliferation.

C-MED-100® treatment was previously shown to accelerate the recovery of blood cells after chemically induced leukopenia in the rat. (Sheng et al. Phytomedicine 2000; 7: 137-43). We have shown that in vivo treatment prolongs lymphocyte half life leading to the accumulation of spleen cells in treated animals. This effect was dependent on the continuous presence of the extract, as lymphocyte numbers regained normal levels within a few weeks of terminating the treatment. As C-MED-100® has a clear anti-apoptotic effect on cells grown in vitro, one may speculate that the accumulation of lymphocytes might be caused by this property of the extract. Further, NF-κB is also known to be involved both in controlling cell division (Chen F, Castranova V, Shi X. New insights into the role of nuclear factor-kappaB in cell growth regulation. Am J Pathol 2001; 159: 387-97; Joyce D, et al. NF-kappaB and cell-cycle regulation: the cyclin connection. Cytokine Growth Factor Rev 2001; 12: 73-90) and cell survival (Mak T W, Yeh W C. Signaling for survival and apoptosis in the immune system. Arthritis Res 2002; 4: S243-52), therefore suggesting that interference with the expression level of this transcriptional regulator might be involved in this in vivo phenomenon.

In plant extracts QA can occur as an ester with caffeic acid, forming chlorogenic acid, a major component in coffee. (Clifford M N. Chlorogenic acids and other cinnamates-nature occurrence and dietary burden. J Sci Food Agric 1999; 79: 362-72). On the other hand, some fruits and berries such as cranberries and sea Buckthorn are particularly rich in free QA. (Coppola E D, Conrad E C, Cotter R. High pressure liquid chromatographic determination of major organic acids in cranberry juice. J Assoc Off Anal Chem 1978; 61: 1490-2; Beveridge T, Harrison J E, Drover J. Processing effects on the composition of sea buckthorn juice from Hippophae rhamnoides L. Cv. Indian Summer. J Agric Food Chem 2002; 50: 113-6). The absorption of dietary chlorogenic acid by both human and rodents is well-documented. (Olthof M R, Hollman P C, Katan M B. Chlorogenic acid and caffeic acid are absorbed in humans. J Nutr 2001; 131: 66-71; Olthof M R, et al. Chlorogenic acid, quercetin-3-rutinoside and black tea phenols are extensively metabolized in humans. J Nutr 2003; 133: 1806-14; Gonthier M P, Verny M A, Besson C, Remesy C, Scalbert A. Chlorogenic acid bioavailability largely depends on its metabolism by the gut microflora in rats. J Nutr 2003; 133: 1853-9). It has been shown that gut microflora play an important role in the absorption of this compound by providing the esterases hydrolyzing chlorogenic acid into its constituents QA and caffeic acid (Gonthier M P, Verny M A, Besson C, Remesy C, Scalbert A. J Nutr 2003; 133: 1853-9; Adamson R H, Bridges J W, Evans M E, Williams R T. Species differences in the aromatization of quinic acid in vivo and the role of gut bacteria. Biochem J 1970; 116: 437-43) components. The QA component could then be subsequently further metabolized in tissues (Gonthier M P, Verny M A, Besson C, Remesy C, Scalbert A. J Nutr 2003; 133: 1853-9).

Based on the foregoing, it is clear that the bioactive agent of C-MED-100® in vivo is not quinic acid lactone, but rather is quinic acid and its salts, including its ammonium salt. Accordingly the effects of C-MED-100®, including enhancing DNA repair, enhancing immune competency, inhibiting the inflammatory response, decreasing the proliferation of leukemic cells, treating immune system disorders, treating disorders associated with the inflammatory response, enhancing the anti-tumor response, treating disorders associated with the response to tumor formation, shown to be attributable to quinic acid analogs, such as quinic acid lactone, in vitro, are attributable as well to quinic acid and quinic acid salts, including ammonium-treated quinic acid, in vivo.

Example 8

Figure 8:
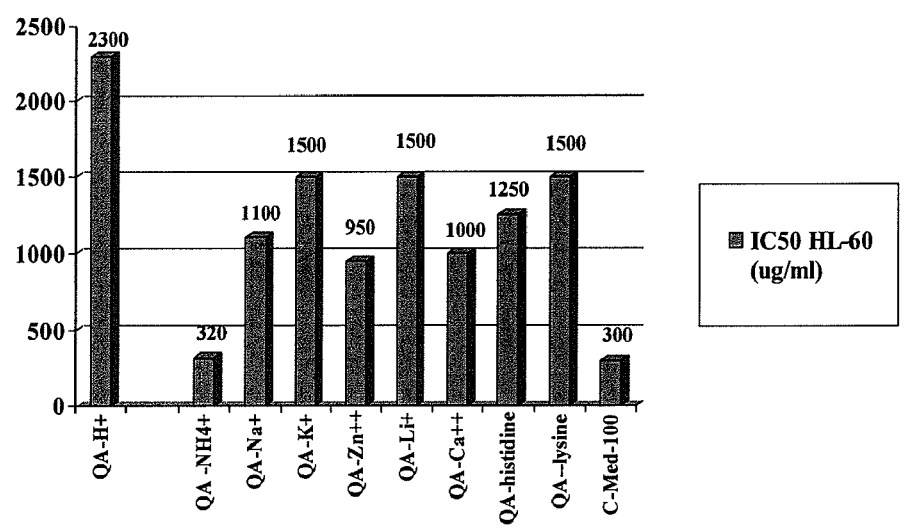
FIG. 8 shows in vitro growth inhibition induced by various QA salts in cultured HL-60 cells, as compared to growth inhibition induced by C-MED-100®.

Turning to FIG. 8, we further disclose that QA salts, especially QAA, were much more bioactive in vitro than QA alone. It is further taught that QA salts can be used to overcome the lack of efficacious comparison between the in vitro and in vivo biological activity data of QA. Further, in order to solve the problem of topical application of QA, we disclose that certain QA salts have in vitro efficacy comparable to that of C-MED-100® itself, thus rendering those QA salts useful for topical administration where systemic metabolism by the liver or the GI tract are not required. Specifically, certain QA salts—including but not limited to QAA, QA zinc salt (QA-Zn), QA calcium salt (QA-Ca) and QA sodium salt (QA-NA)—exhibit an $IC_{50}$ in cultured HL-60 cells of no greater than 1,100 µg/ml, comparable to the $IC_{50}$ value for C-MED-100® and less than the $IC_{50}$ value for QAL. It is thus disclosed herein that certain QA salts, such as QAA-QA-Zn, QA-Ca and QA-Na, are biologically effective both in vitro and in vivo, whereas QA is bioactive only in vivo.

QA was purchased from Sigma (>99%). QA salts were synthesized by neutralization with the appropriate base, i.e., $NH_4OH$, $NaOH$, $Ca(OH)_2$, $Zn(OH)_2$, LiOH, KOH, lysine or histidine. Serial dilutions of test compounds were added to human HL-60 leukemic cells ($0.05 \times 10^6$ cells/ml) in 96-well, flat bottomed microtiter plates to give final concentrations in the cultures up to 3000 µg/ml. The plates were incubated for 72 hr at 37 C, pulsed with 20 µl MTT (5 mg/ml) for 3 hr, and the color estimated spectrophotometrically at 540 nm as described previously. (Schweitzer, C M et al. Spectrophotometric determination of clonogenic capacity of leukemic cells in semisolid microtiter culture systems. Experimental Hematology 21: 573-578, 1993). $IC_{50}$ values were calculated and compared based on the live/dead ratio of cells.

As shown in FIG. 8, QA alone shows a much greater in vitro cytotoxicity than does C-MED-100®. By contrast, certain QA salts, in particular QAA (denoted in FIG. 8 as QA-$NH_4^+$), QA-Zn, QA-Ca and QA-Na, show an in vitro cytotoxicity comparable to that of C-MED-100®. Indeed, of the eight (8) QA salts tested, QAA showed an in vitro cytotoxicity level closest to that of C-MED-100®. Turning to Table 2, QAA, QA-Zn, QA-Ca and QA-Na are shown to have even less cytotoxicity in vitro that QAL, which is known to be the in vitro biologically active component of C-MED-100®. As a result, QAA may show bioactivity in vitro comparable to that of C-MED-100®, in addition to its bioactivity in vivo. These QA salts thus may be useful in topical applications, where systemic conversion of QAL or C-MED-100® to QA is neither necessary nor desired. These salts thus may be applied topically, to achieve the beneficial results ascribed to C-MED-100®.

While the invention has been described with respect to certain specific embodiments, it will be appreciated that many modifications and changes may be made by those skilled in the art without departing from the invention. It is intended, therefore, by the appended to cover all such modifications and changes as may fall within the true spirit and scope of the invention.

What is claimed is:

1. A method for enhancing the DNA repair process of a mammal in need thereof comprising administering to said mammal a pharmaceutical composition comprising a compound selected from the group consisting of a quinic acid and a quinic acid salt, in an amount effective to inhibit TNF-α production or to induce apoptosis of white blood cells, where said quinic acid and said quinic acid salt may form an ammonium salt and/or chelate thereof having a bioassay efficacy using $IC_{50}$ in HL-60 cells of approximately 500 µg/ml or less, and where said administration is other than topical.

2. The method of claim 1 wherein said amount is effective to inhibit TNF-α production.

3. The method of claim 1 wherein said amount is effective to induce apoptosis of white blood cells.

4. The method of claim 1 wherein said administering includes a nontoxic inert carrier.

5. The method of claim 1 wherein said administering includes a diluent.

6. A method for treating disorders associated with the DNA repair process of a mammal in need thereof by administering to said mammal a pharmaceutical composition comprising a compound selected from the group consisting of a quinic acid and a quinic acid salt, in an amount effective to inhibit TNF-α production or to induce apoptosis of white blood cells, where said quinic acid and said quinic acid salt may form an ammonium salt and/or chelate thereof having a bioassay efficacy using $IC_{50}$ in HL-60 cells of approximately 500 µg/ml or less, and where said administration is other than topical.

7. The method of claim 6 wherein said amount is effective to inhibit TNF-α production.

8. The method of claim 6 wherein said amount is effective to induce apoptosis of white blood cells.

9. The method of claim 6 wherein said administering includes a nontoxic inert carrier.

10. The method of claim 6 wherein said administering includes a diluent.

* * * * *